(12) United States Patent
Masuda

(10) Patent No.: US 11,446,173 B2
(45) Date of Patent: Sep. 20, 2022

(54) SLEEP APNEA SYNDROME SYMPTOM IMPROVEMENT AID

(71) Applicant: SOUKEN CO., LTD., Hiroshima (JP)

(72) Inventor: Hiroto Masuda, Hiroshima (JP)

(73) Assignee: SOUKEN CO., LTD., Hiroshima (JP)

( * ) Notice: Subject to any disclaimer, the term of this patent is extended or adjusted under 35 U.S.C. 154(b) by 922 days.

(21) Appl. No.: 16/317,550

(22) PCT Filed: Jul. 10, 2018

(86) PCT No.: PCT/JP2018/026079
§ 371 (c)(1),
(2) Date: Jan. 13, 2019

(87) PCT Pub. No.: WO2019/130628
PCT Pub. Date: Jul. 4, 2019

(65) Prior Publication Data
US 2021/0369496 A1    Dec. 2, 2021

(30) Foreign Application Priority Data

Dec. 26, 2017   (JP) .............................. JP2017-248996

(51) Int. Cl.
*A61B 5/1455*    (2006.01)
*A61B 5/00*    (2006.01)
(Continued)

(52) U.S. Cl.
CPC .............. *A61F 5/56* (2013.01); *A61B 5/0261* (2013.01); *A61B 5/02433* (2013.01);
(Continued)

(58) Field of Classification Search
CPC . A61B 5/0205; A61B 5/0261; A61B 5/02433; A61B 5/4818; A61B 5/02416;
(Continued)

(56) References Cited

U.S. PATENT DOCUMENTS 5,205,281 A * 4/1993 Buchanan .......... A61B 5/14552
128/207.14
5,590,643 A * 1/1997 Flam ................. A61M 16/0488
128/207.14
(Continued)

FOREIGN PATENT DOCUMENTS

| CN | 1484517 A | 3/2004 |
|---|---|---|
| CN | 105726192 A | 7/2016 |

(Continued)

OTHER PUBLICATIONS

International Search Report and Written Opinion for International App. No PCT/JP2018/026079, dated Sep. 25, 2018.

*Primary Examiner* — Chu Chuan Liu
(74) *Attorney, Agent, or Firm* — Renner, Otto, Boisselle & Sklar, LLP

(57) ABSTRACT

A sleep apnea syndrome symptom improvement aid 1 includes a sandwiching target 10 sandwiched by front teeth of a patient, a tongue presser 20 extending from the sandwiching target 10 to the vicinity of the soft palate of the patient and including an elastic body configured to press the tongue, and a detector 30 configured to detect at least one of a vital sign or a salivary component of the patient.

8 Claims, 26 Drawing Sheets

(51) Int. Cl.
  *A61F 5/56* (2006.01)
  *A61B 5/024* (2006.01)
  *A61B 5/026* (2006.01)
  *A61B 10/00* (2006.01)

(52) U.S. Cl.
  CPC ........ *A61B 5/14551* (2013.01); *A61B 5/4277* (2013.01); *A61B 5/4818* (2013.01); *A61B 10/0051* (2013.01); *A61B 2562/0238* (2013.01)

(58) Field of Classification Search
  CPC .............. A61B 5/1455; A61B 5/11451; A61B 5/14552; A61B 5/14532; A61B 5/0002; A61B 5/682; A61B 2562/0238
  See application file for complete search history.

(56) References Cited

U.S. PATENT DOCUMENTS

| | | |
|---|---|---|
| 6,675,804 B1 | 1/2004 | Pivovarov |
| 2003/0192549 A1 | 10/2003 | Boussignac |
| 2009/0123886 A1 | 5/2009 | Vaska |
| 2017/0211438 A1 | 7/2017 | Suzuki |
| 2017/0312117 A1* | 11/2017 | Shah .................. A61B 5/14552 |
| 2018/0263809 A1 | 9/2018 | Masuda |

FOREIGN PATENT DOCUMENTS

| | | |
|---|---|---|
| JP | 2013-106811 A | 6/2013 |
| JP | 2016-034411 A | 3/2016 |
| JP | 2016-093397 A | 5/2016 |
| JP | 2017-104308 A | 6/2017 |

\* cited by examiner

SLEEP APNEA SYNDROME SYMPTOM IMPROVEMENT AID

TECHNICAL FIELD

The present invention relates to a tool for assisting improvement of a symptom of a sleep apnea syndrome, and particularly belongs to a technical field of a structure of a tool used with the tool being inserted into the mouth during sleeping.

BACKGROUND ART

Normally, in a case where a posture in bedtime is a supine position, when body muscles relax during sleeping, a tongue root portion tends to move downward due to influence of the force of gravity. When the moved-down tongue closes the respiratory passage, an apnea state might be brought. This is a symptom of a sleep apnea syndrome.

For example, a continuous positive airway pressure (CPAP) device has been known as a device for improving the symptom of the sleep apnea syndrome (see, e.g., Patent Document 1). The CPAP device is configured such that a mask or a nasal prong is attached to the face and air is forcibly sent into the respiratory passage by a fan. Specifically, a housing including a built-in air blower fan is placed at a location apart from a patient, and the housing and the mask attached to the face are connected to each other via a hose. Air is sent into the respiratory passage of the patient by way of the hose, and in this manner, the symptom of the sleep apnea syndrome is improved.

Masks of CPAP devices in various shapes are available in the market, and the patient can optionally select and use, e.g., a mask matching the shape of the face of the patient oneself or a patient's preference. However, there is an uncomfortable feeling due to attachment of the mask to the face, and there is also an uncomfortable feeling due to the hose constantly present in the vicinity of the face. These feelings might interfere with sleeping. Further, a motor configured to drive the face and a power source configured to supply power to the motor are necessary. This leads to a large-scale device, and therefore, leads to a cost increase.

For these reasons, as disclosed in, e.g., Patent Documents 2 to 4, a tool to be inserted into the mouth during sleeping has been known as a tool providing less uncomfortable feeling than the CPAP device and configured to improve the symptom of the sleep apnea at low cost.

The tool disclosed in Patent Document 2 includes an arch portion holding a damping member contacting the soft palate and curved along the palate, and a pair of jaw passing portions each arranged at both of right and left ends of the arch portion and housed in right and left retromolar gaps. At the jaw passing portion, an arm portion bending forward and housed in the vestibule of the mouth is formed. Further, a reaction plate curved along the soft palate is fixed to the arch portion, and due to reactive force of the relation plate, the tongue less moves down during sleeping.

The tool disclosed in each of Patent Document 3 and 4 includes an elastic body to be inserted into the mouth. A front end portion of the tool has a sandwiching target to be sandwiched by the front teeth in an upper-to-lower direction, and a back end portion of the tool is formed to extend close to the soft palate. The tongue is pushed by the vicinity of the back end portion of this tool, and therefore, the tongue less moves down during sleeping.

CITATION LIST

Patent Document

PATENT DOCUMENT 1: Japanese Unexamined Patent Publication No. 2016-034411
PATENT DOCUMENT 2: Japanese Unexamined Patent Publication No. 2013-106811
PATENT DOCUMENT 3: Japanese Unexamined Patent Publication No. 2017-104308
PATENT DOCUMENT 4: Japanese Unexamined Patent Publication No. 2016-093397

SUMMARY OF THE INVENTION

Technical Problem

Using the sleep apnea syndrome symptom improvement aid inserted into the mouth as in Patent Documents 2 to 4, improvement of the symptom of the sleep apnea syndrome is expected without use of the large-scale CPAP device including the fan, the motor, the power source, etc. as in Patent Document 1.

However, the typical sleep apnea syndrome symptom improvement aid has been developed only for the purpose of improving the symptom of the sleep apnea syndrome, and has been used only for improving the symptom of the sleep apnea syndrome.

The symptom of the sleep apnea syndrome patient might suddenly worsen even when the sleep apnea syndrome symptom improvement aid is used, and for promptly recognizing such a state, there is a demand for detecting a vital sign during sleeping. The vital sign includes, for example, a body temperature, a heart rate, a pulse, a blood pressure, and a blood oxygen level, and is a signal indicating that a human is alive and indicating whether or not a human is in a normal state.

In recent years, multiple biomarkers measurable from the saliva have been found. A component in the saliva is analyzed, and the level of each biomarker is measured. In this manner, various symptoms can be early discovered.

In the saliva, an extremely-small amount of glucose with respect to the blood is contained, and the amount of glucose contained in the saliva is measured so that a blood glucose level can be estimated. That is, the saliva is collected instead of the blood so that diabetes can be diagnosed.

The present invention has been made in view of the above-described points, and an object of the present invention is to improve a symptom of a sleep apnea syndrome by a sleep apnea syndrome symptom improvement aid while less-invasive detection of a vital sign is allowed and detection of a component contained in the saliva is allowed.

Solution to the Problem

For accomplishing the above-described object, a detector configured to detect a vital sign or a component in the saliva is, in the present invention, provided at a sleep apnea syndrome symptom improvement aid.

A first aspect is a sleep apnea syndrome symptom improvement aid to be inserted into the mouth of a sleep apnea syndrome patient, the sleep apnea syndrome symptom improvement aid including a sandwiching target which is sandwiched by upper and lower front teeth of the patient and which includes an elastic body arranged facing the outside of the mouth from the lip and having an air passage extending from a front end portion to the inside of the mouth, a tongue presser extending from the sandwiching target to the vicinity of the soft palate of the patient and including an elastic body configured to press the tongue, and a detector provided at at least one of the sandwiching target or the tongue presser and configured to detect at least one of a vital sign or a salivary component of the patient.

According to this configuration, the sleep apnea syndrome symptom improvement aid is inserted into the mouth of the sleep apnea syndrome patient, and the sandwiching target is bitten with the upper and lower front teeth such that the sleep apnea syndrome symptom improvement aid is fixed in the mouth. In this state, oral breathing is allowed via the air passage. Moreover, the tongue presser is positioned to extend to the vicinity of the soft palate of the patient, and therefore, the tongue presser presses the tongue when the sleep apnea syndrome symptom improvement aid is fixed in the mouth. Thus, even when a posture in the bedtime is a supine position, the tongue less moves downward. Thus, a symptom of a sleep apnea syndrome is improved.

A large portion of the sandwiching target is positioned in the mouth, and the entirety of the tongue presser is positioned in the mouth. Thus, the detector is provided at at least one of the sandwiching target or the tongue presser so that the vital sign such as the pulse or the blood oxygen level can be detected in the mouth. Consequently, the state of the patient can be promptly and reliably obtained. Moreover, the detector can detect the salivary component such as a biomarker or glucose.

A second aspect is characterized in that the sandwiching target is provided with a recess into which the front teeth are to be inserted.

According to this configuration, when the sandwiching target is bitten with the upper and lower front teeth, the front teeth are inserted into the recess, and are fitted in the recess. Thus, position shift of the sandwiching target less occurs, and therefore, the effect of improving the symptom of the sleep apnea syndrome is further enhanced.

A third aspect is characterized in that the tongue presser includes a core member.

According to this configuration, the strength of the sandwiching target is enhanced by the core member, and therefore, pressing force of the tongue is enhanced.

A fourth aspect is characterized in that the tongue presser includes an outer layer portion made of elastomer, and the core member is made of a material harder than the elastomer forming the outer layer portion and is embedded in the outer layer portion.

According to this configuration, the core member is covered with the elastomer. Thus, when the sleep apnea syndrome symptom improvement aid is inserted into the mouth, an uncomfortable feeling due to contact of the core member with, e.g., a mucous membrane can be eliminated.

A fifth aspect is characterized in that the detector is provided at the tongue presser.

According to this configuration, the tongue presser presses the tongue, and therefore, e.g., a detector capable of measuring the blood flow of the tongue is provided at the tongue presser so that the pulse, the blood oxygen level, etc. can be accurately measured using the blood flow of the tongue.

A sixth aspect is characterized in that the tongue presser includes a pressing plate portion arranged above the tongue and a lower plate portion arranged below the tongue.

According to this configuration, when the sleep apnea syndrome symptom improvement aid is inserted into the mouth of the patient, the tongue can be inserted into a portion between the pressing plate portion and the lower plate portion of the tongue presser. Thus, relative position relationship between the tongue and the sleep apnea syndrome symptom improvement aid less shifts, and the effect of improving the symptom of the sleep apnea syndrome is enhanced.

A seventh aspect is characterized in that the detector includes an irradiator arranged at one of the pressing plate portion or the lower plate portion and configured to irradiate the tongue with light and a light receiver arranged at the other one of the pressing plate portion or the lower plate portion and configured to receive the light irradiated from the irradiator, and the detector is configured to obtain the blood flow of the tongue based on the intensity of light received by the light receiver.

According to this configuration, the light irradiated from above or below the tongue by the irradiator is received by the light receiver through the tongue. The intensity of light received by the light received varies according to a change in a blood flow rate or the presence or absence of the blood flow. Thus, the blood flow of the tongue can be obtained based on the received light intensity.

An eighth aspect is characterized in that the tongue presser includes a support rod configured to swingably support the lower plate portion in an upper-to-lower direction and a biasing member configured to bias the lower plate portion in the direction of pressing the lower plate portion against a lower side of the tongue.

According to this configuration, the lower plate portion is swung against biasing force of the biasing member in the direction away from the pressing plate portion, and therefore, the tongue can be easily inserted into the portion between the pressing plate portion and the lower plate portion. After the tongue has been inserted into the portion between the pressing plate portion and the lower plate portion, the lower plate portion is pressed against the lower side of the tongue by the biasing force of the biasing member. Thus, relatively position relationship between the tongue and the sleep apnea syndrome symptom improvement aid less shifts, and the effect of improving the symptom of the sleep apnea syndrome is enhanced.

A ninth aspect is characterized by further including a transmitter configured to transmit a detection result of the detector to the outside.

According to this configuration, the result of detection by the detector is transmitted to the outside by the transmitter, and therefore, a medical profession can check the vital sign etc. by means of an external terminal at a hospital etc. Moreover, the patient oneself can check the vital sign etc.

A tenth aspect is characterized in that the tongue presser is provided with a saliva reservoir configured to accumulate saliva and the detector configured to detect the salivary component is provided at the saliva reservoir.

According to this configuration, the component in the saliva accumulated in the saliva reservoir can be reliably detected by the detector.

Advantages of the Invention

According to the present invention, the sleep apnea syndrome symptom improvement aid includes the detector configured to detect at least one of the vital sign or the salivary component of the patient. Thus, the symptom of the sleep apnea syndrome can be improved while less-invasive detection of the vital sign is allowed. Moreover, the component contained in the saliva can be detected.

DESCRIPTION OF EMBODIMENTS

Hereinafter, embodiments of the present invention will be described in detail with reference to the drawings. Note that preferred embodiments below will be set forth merely as examples in nature, and are not intended to limit the present invention and applications or use thereof.

First Embodiment

Figure 1:
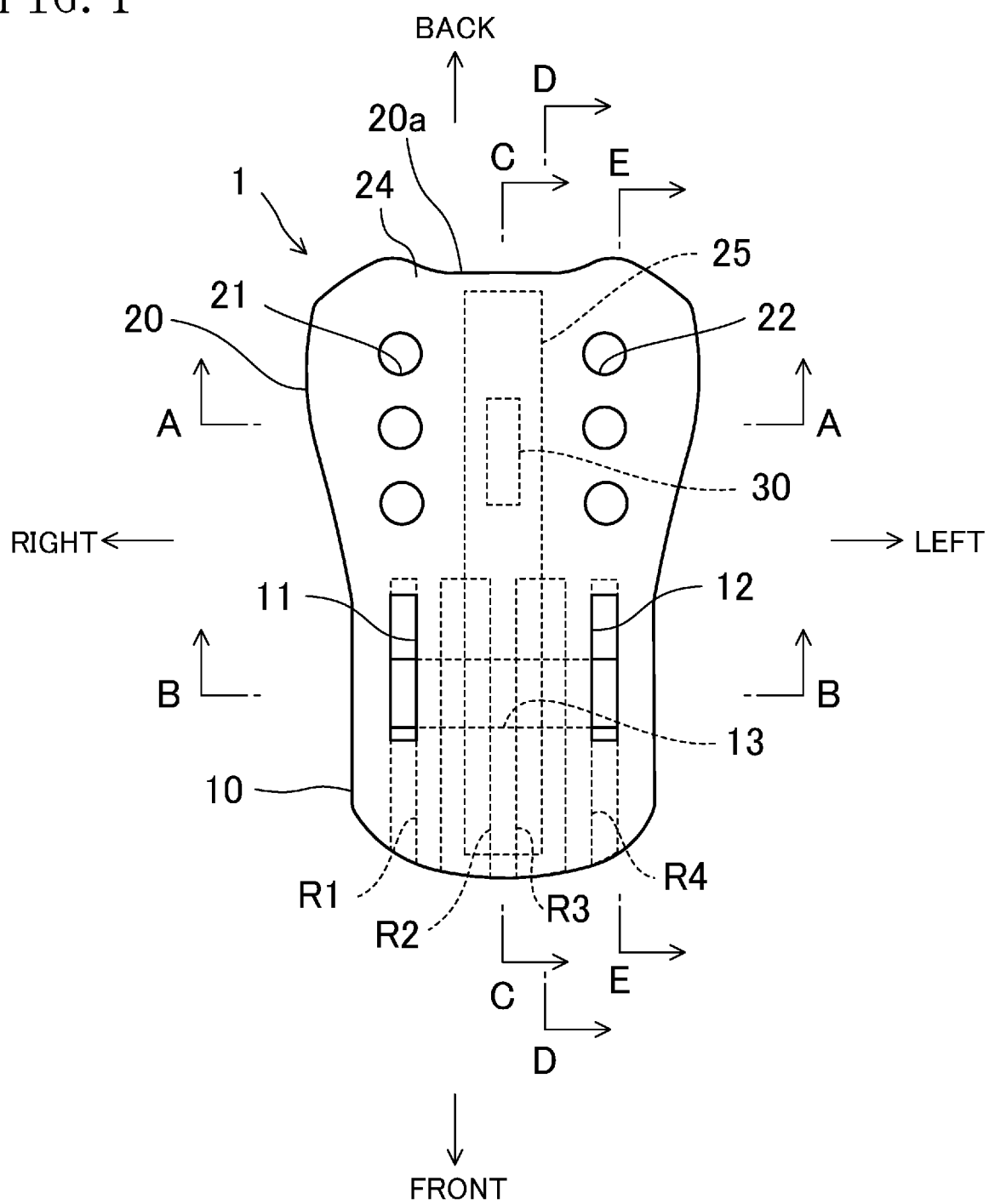
FIG. 1 is a plan view of a sleep apnea syndrome symptom improvement aid according to a first embodiment.
Figure 2:
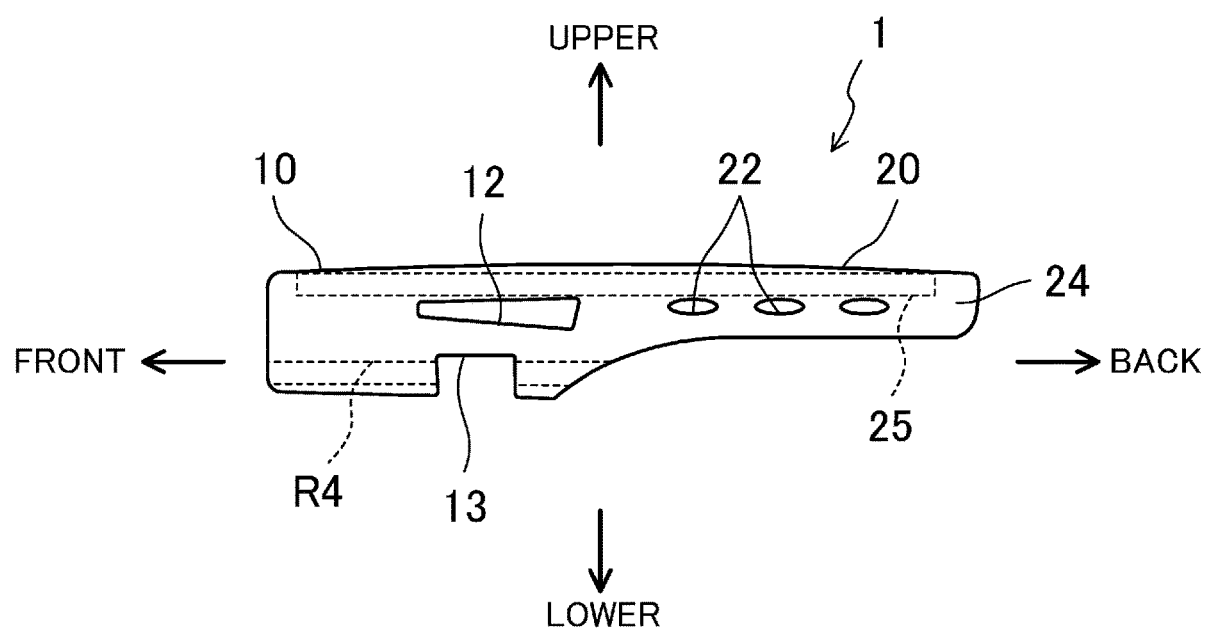
FIG. 2 is a left side view of the sleep apnea syndrome symptom improvement aid.
Figure 3:
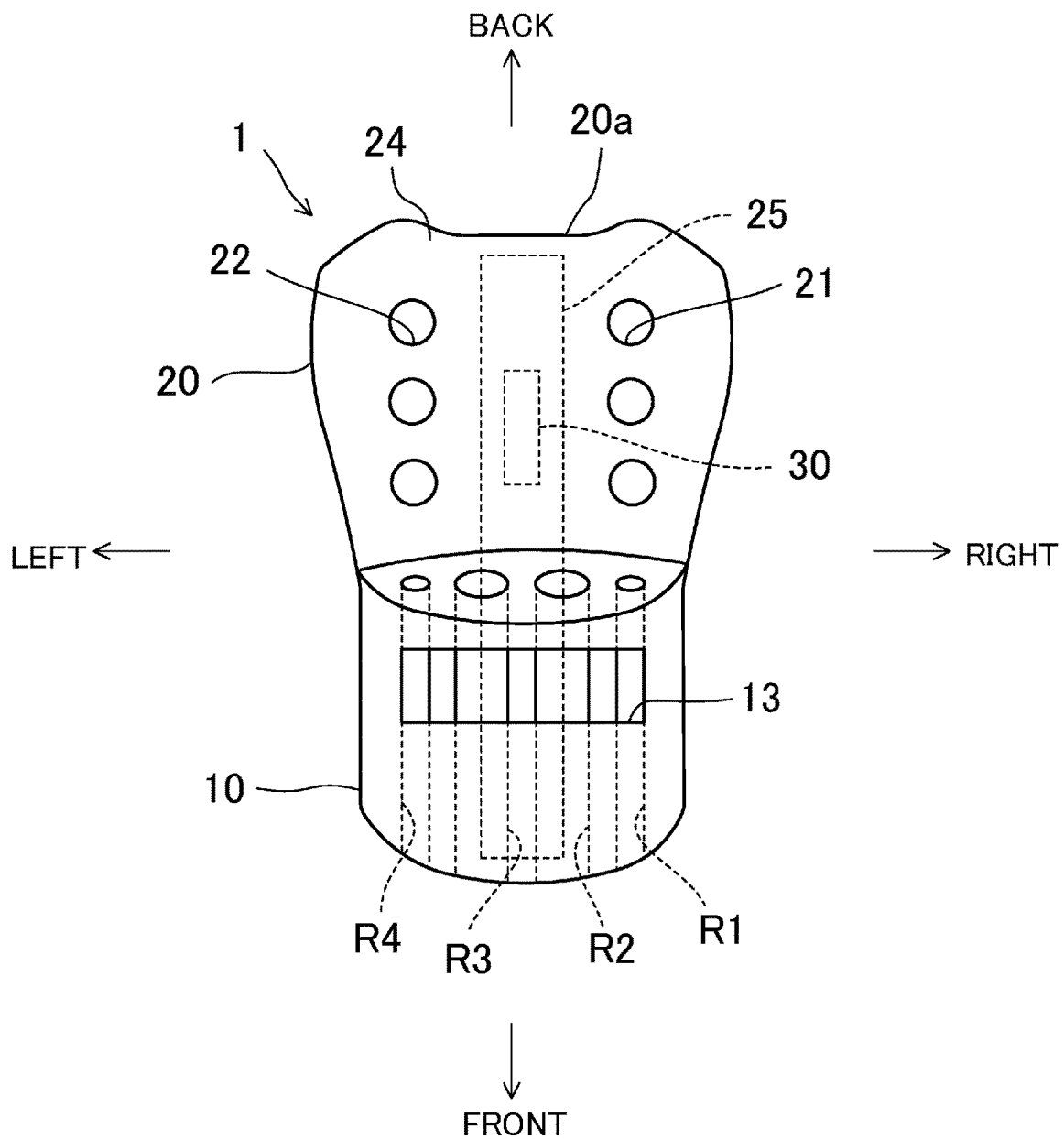
FIG. 3 is a bottom view of the sleep apnea syndrome symptom improvement aid.
Figure 4:
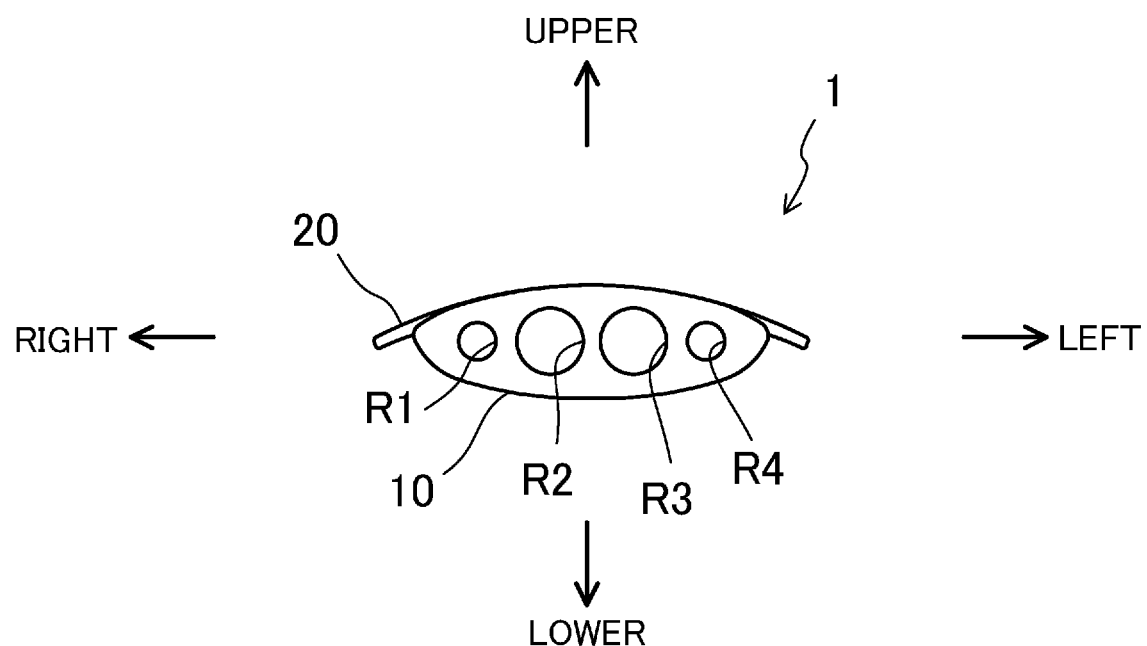
FIG. 4 is a front view of the sleep apnea syndrome symptom improvement aid.
Figure 12:
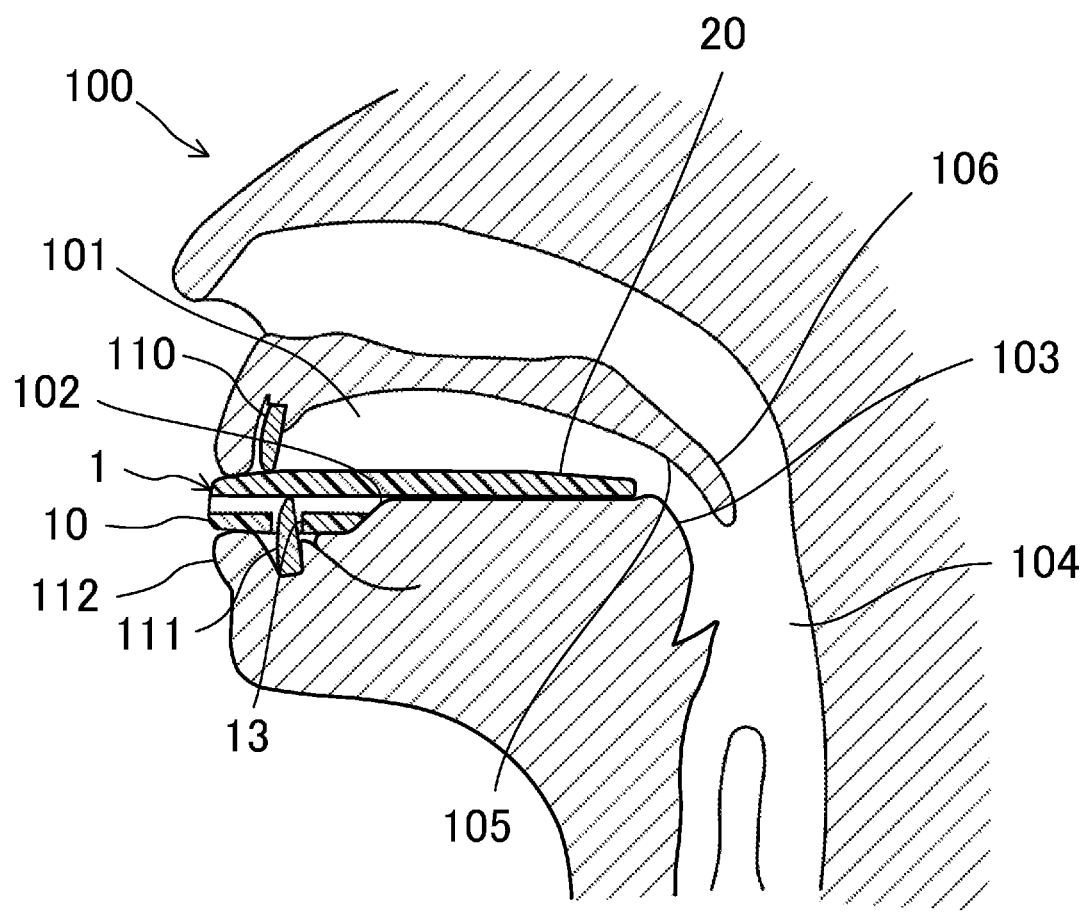
FIG. 12 is a view for describing the vicinity of the throat of a patient in a state in which the sleep apnea syndrome symptom improvement aid is inserted.

FIG. 1 is a plan view of a sleep apnea syndrome symptom improvement aid 1 according to a first embodiment of the present invention, FIG. 2 is a left side view, FIG. 3 is a bottom view, and FIG. 4 is a front view. As illustrated in FIG. 12, the sleep apnea syndrome symptom improvement aid 1 is inserted into the mouth 101 of a sleep apnea syndrome patient 100. In description of this embodiment, in a state in which the sleep apnea syndrome symptom improvement aid 1 is inserted into the mouth 101, a near side (an upper side in FIG. 12) in an insertion direction will be referred to as a "front," and a far side (a lower side in FIG. 12) in the insertion direction will be referred to as a "back."

Moreover, in a state in which the sleep apnea syndrome symptom improvement aid 1 is inserted into the mouth 101, the right side of the patient 100 will be merely referred to as a "right," and the left side of the patient 100 will be merely referred to as a "left."

Figure 11:
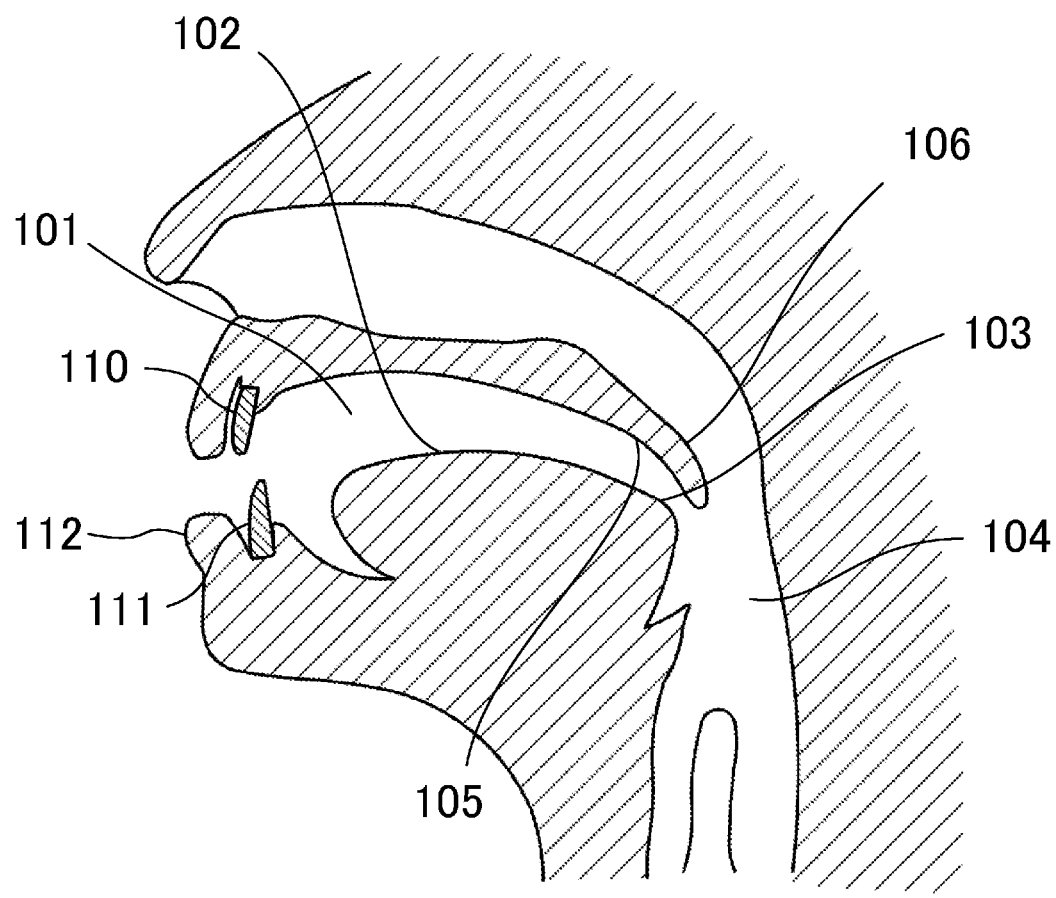
FIG. 11 is a view for describing the vicinity of the throat of a normal individual in a supine position during sleeping.

Generally, in bedtime, body muscles relax when a sleep state is brought. In bedtime, in the case of a normal individual, when the sleep state is brought in a supine position, a tongue root portion 103 as a back portion of the tongue 102 does not move down and does not close the respiratory passage 104 of the throat as illustrated in FIG. 11. On the other hand, in the case of the sleep apnea syndrome patient, muscles functioning to change the position of the tongue root portion 103 relax, and due to influence of the force of gravity, the tongue root portion 103 moves down and closes the respiratory passage 104 of the throat. In this state, the soft palate 105 or the uvula 106 might also move down and close the respiratory passage 104 of the throat. When the respiratory passage 104 is closed, air needing to flow into the lung is blocked, and therefore, a sleep apnea syndrome occurs.

The muscles functioning to change the position of the tongue 102 is called extrinsic muscles. The extrinsic muscles include the styloglossus muscle for pulling the tongue backward, the hyoglossal muscle for pulling the tongue downward, the palatoglossal muscle contacting a lateral margin of the tongue to lift the dorsum of the tongue, and the genioglossus muscle for moving the tongue to protrude forward. Of these muscles, the styloglossus muscle, the hyoglossal muscle, and the palatoglossal muscle are muscles greatly influencing the tongue root portion 103 as the back portion of the tongue. In bedtime, when the sleep state is brought, the body muscles relax, and therefore, these muscles also relax.

The sleep apnea syndrome symptom improvement aid 1 includes a sandwiching target 10 which is sandwiched by upper front teeth 110 and lower front teeth 111 (illustrated in FIG. 12) of the patient 100 and which has an elastic body arranged facing the outside of the mouth 101 from the lip 112 and provided with air passages R1 to R4 extending from a front end portion to the inside of the mouth 101, a tongue presser 20 extending from the sandwiching target 10 to the vicinity of the soft palate 105 of the patient 100 and having an elastic body configured to press the tongue 102, and a detector 30 (illustrated in FIG. 1 etc.) provided at at least one of the sandwiching target 10 or the tongue presser 20 and configured to detect at least one of a vital sign or a salivary component of the patient.

The sandwiching target 10 and the tongue presser 20 of the sleep apnea syndrome symptom improvement aid 1 may be integrally molded, but the present invention is not limited to above. For example, the sandwiching target 10 and the tongue presser 20 may be separately molded, and thereafter, may be integrated by a method such as welding, adhesive bonding, or coupling. The sandwiching target 10 and the tongue presser 20 can be obtained by injection molding or a 3D printer, for example.

The sandwiching target 10 and the tongue presser 20 of the sleep apnea syndrome symptom improvement aid 1 may be made of the same material, or may be made of different materials. The materials forming the sandwiching target 10 and the tongue presser 20 may be elastic bodies exhibiting flexibility, and for example, may include synthetic rubber and synthetic resin foam (elastomer). Of these materials, physiologically-safe silicone rubber having almost no smell is most suitable. When the thicknesses of the sandwiching target 10 and the tongue presser 20 are extremely small, the sandwiching target 10 and the tongue presser 20 are difficult to push and balloon the cheek outward and to secure the respiratory passage 104. On the other hand, when the thicknesses of the sandwiching target 10 and the tongue presser 20 are extremely great, the flexibility is lowered, and rubber hardness becomes higher. Thus, it is difficult to easily curve the sandwiching target 10 and the tongue presser 20, and therefore, it is difficult to insert the sandwiching target 10 and the tongue presser 20 into the mouth 101. For these reasons, the thicknesses of the sandwiching target 10 and the tongue presser 20 are suitably set to equal to or greater than 2 mm, and preferably around 5 mm. Moreover, the rubber hardness of the materials of the sandwiching target 10 and the tongue presser 20 is preferably about 8 to 13 degrees.

As illustrated in, e.g., FIGS. 1 to 4, the sandwiching target 10 of the sleep apnea syndrome symptom improvement aid 1 has a flat section elongated in a right-to-left direction. In a state in which the sleep apnea syndrome symptom improvement aid 1 is inserted into the mouth 101 as illustrated in FIG. 12, the front end portion of the sandwiching target 10 is a portion arranged facing the outside of the mouth 101 from a portion between the upper lip and the lower lip. One end portions (front end portions) of the air passages R1 to R4 open at the front end portion of the sandwiching target 10. Thus, the air passages R1 to R4 are configured so that air can be taken in from the outside of the mouth 101.

Figure 7:
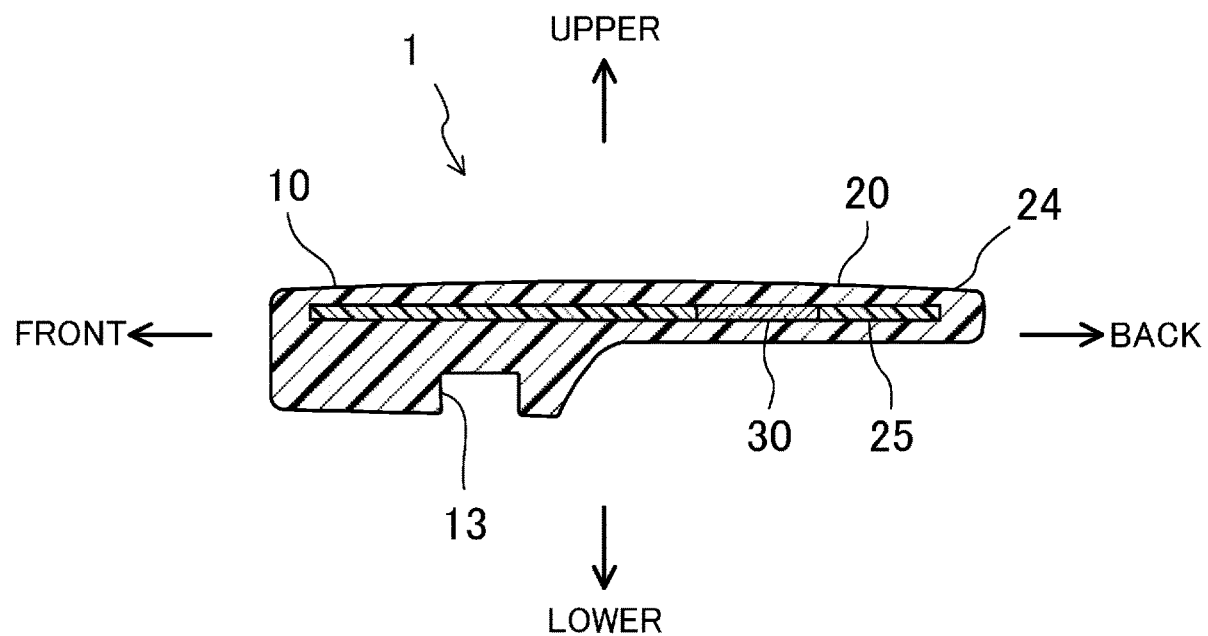
FIG. 7 is a sectional view along a C-C line of FIG. 1.
Figure 8:
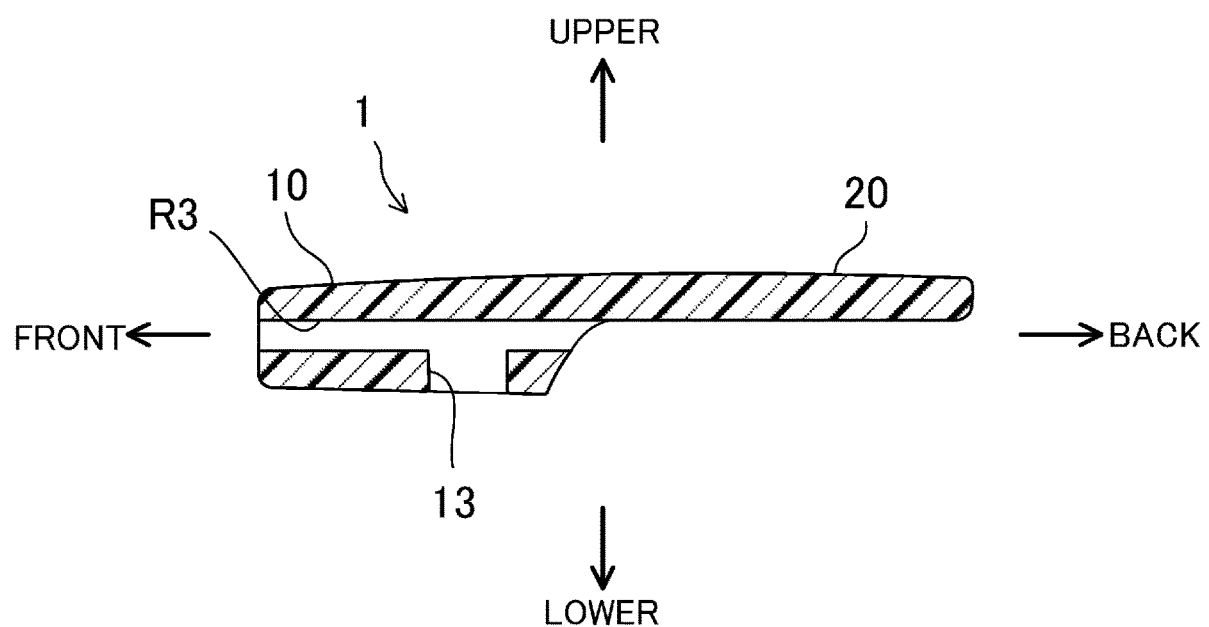
FIG. 8 is a sectional view along a D-D line of FIG. 1.
Figure 9:
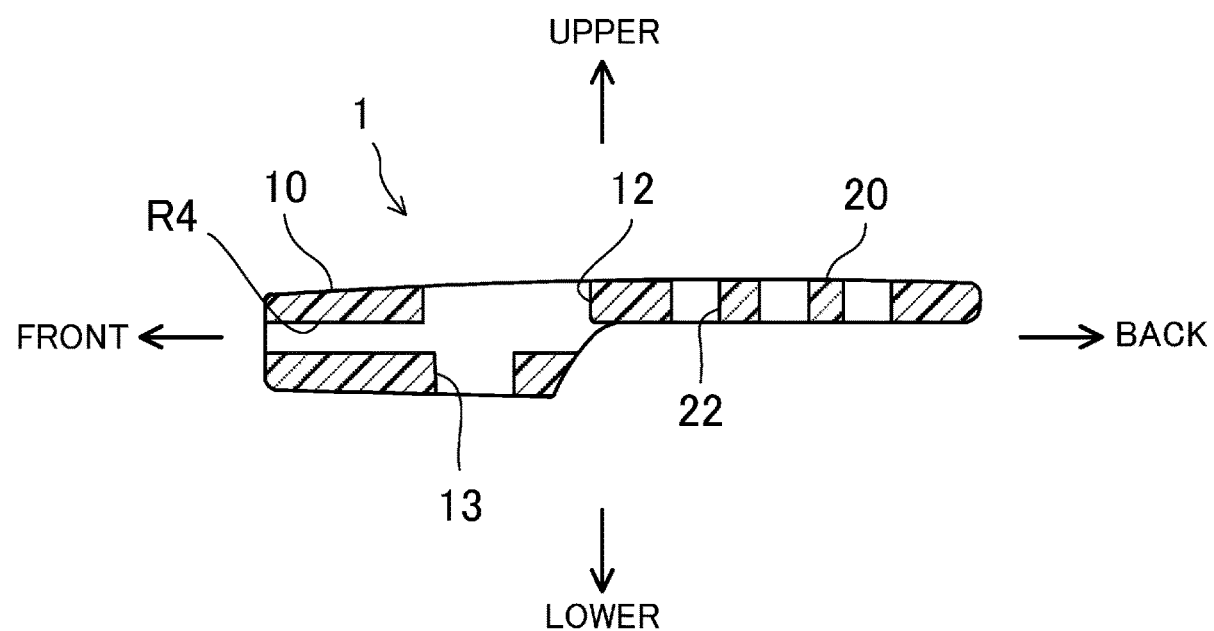
FIG. 9 is a sectional view along an E-E line of FIG. 1.

As illustrated in FIGS. 7 to 9, the sandwiching target 10 is formed across an area from a front end portion to a middle portion of the sleep apnea syndrome symptom improvement aid 1 in a front-to-back direction. A back portion of the sleep apnea syndrome symptom improvement aid 1 with respect to the tongue presser 20 is the tongue presser 20. An area where the sandwiching target 10 is formed and an area where the tongue presser 20 is formed can be set as necessary. Moreover, the length of the sandwiching target 10 in the front-to-back direction and the length of the tongue presser 20 in the front-to-back direction may be different from each other, or may be the same as each other. The length of the sandwiching target 10 in the front-to-back direction and the length of the tongue presser 20 in the front-to-back direction can be set according to, e.g., the body type of the patient 100 or the symptom of the sleep apnea syndrome. The length of the sandwiching target 10 in the front-to-back direction may be longer than that of the tongue presser 20, or may be shorter than that of the tongue presser 20.

As illustrated in FIG. 7, the dimension (the thickness) of the sandwiching target 10 in an upper-to-lower direction is greater than that of the tongue presser 20. This is for forming the air passages R1 to R4 at the sandwiching target 10 and easily biting and holding the sandwiching target 10 with the upper front teeth 110 and the lower front teeth 111 (illustrated in FIG. 12). A back end surface of the sandwiching target 10 is an inclined surface positioned forward as extending downward.

As illustrated in FIG. 1, the air passage R1 is provided on the right side of the sandwiching target 10, and extends in the front-to-back direction. The air passage R2 is provided apart leftward from the air passage R1, and extends substantially parallel to the air passage R1. The air passage R3 is provided apart leftward from the air passage R2, and extends substantially parallel to the air passages R1, R2. The air passage R4 is provided apart leftward from the air passage R3, and is provided on the left side of the sandwiching target 10. Moreover, the air passage R4 extends substantially parallel to the air passages R1 to R3. In this embodiment, four air passages including the air passages R1 to R4 are provided, but the present invention is not limited to above. For example, one, two, or three air passages may be provided, and five or more air passages may be provided. The diameters of the air passages R1 to R4 can be set as necessary.

The other end portions (back end portions) of the air passages R1 to R4 open at the back end surface of the sandwiching target 10. In a state in which the sleep apnea syndrome symptom improvement aid 1 is inserted into the mouth 101 as illustrated in FIG. 12, the other end portions of the air passages R1 to R4 open inside the mouth 101. Thus, the inside and outside of the mouth 101 communicate with each other via the air passages R1 to R4, and therefore, the patient 100 can breathe through the mouth by means of the air passages R1 to R4.

At the sandwiching target 10, a right communication hole 11 communicating with the air passage R1 and a left communication hole 12 communicating with the air passage R4 are formed. The right communication hole 11 communicates with a middle portion of the air passage R1 in the front-to-back direction, and opens at an upper surface of the sandwiching target 10. The left communication hole 12 communicates with a middle portion of the air passage R4 in the front-to-back direction, and opens at the upper surface of the sandwiching target 10. Thus, the air passages R1, R4 open upward. Note that communication holes communicating with the air passages R2, R3 may be provided.

Figure 6:
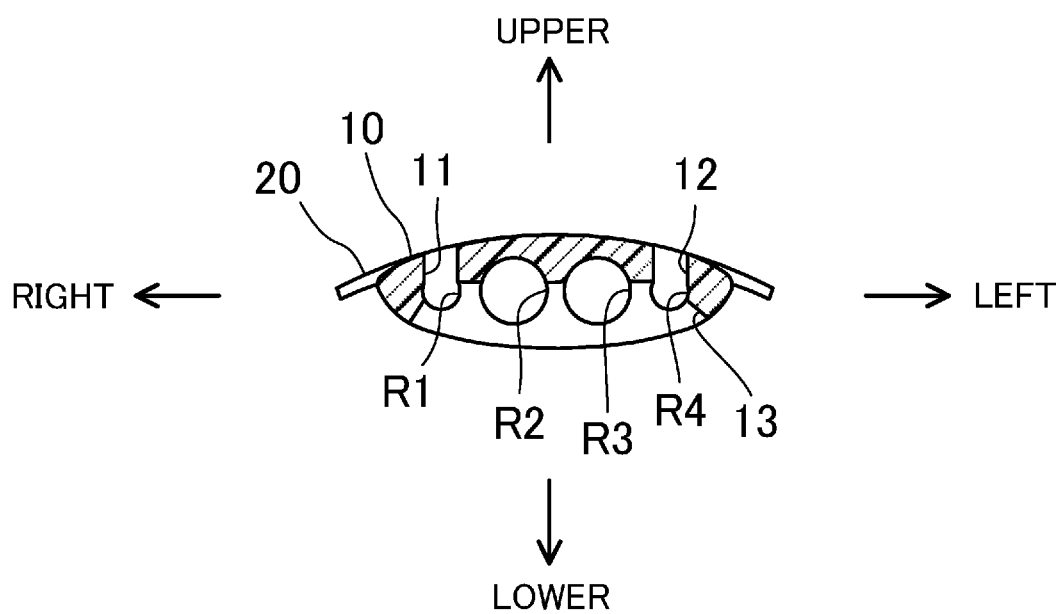
FIG. 6 is a sectional view along a B-B line of FIG. 1.

A front teeth insertion recess 13 into which the lower front teeth 111 of the patient 100 are to be inserted as illustrated in FIG. 12 is formed at the sandwiching target 10. As illustrated in, e.g., FIGS. 2 and 3, the front teeth insertion recess 13 opens at a lower surface of the sandwiching target 10, and the lower front teeth 111 of the patient 100 can be inserted through such an opening portion. The front teeth insertion recess 13 is formed from the right side to the left side of the sandwiching target 10. Moreover, the dimension of the front teeth insertion recess 13 in the front-to-back direction is set so that at least two or more lower front teeth 111 can be inserted, considering the thickness of the lower front tooth 111 of a general adult and arrangement of the front teeth 111 of the general adult. As illustrated in FIG. 6, the front teeth insertion recess 13 communicates with the air passages R1 to R4. Thus, air in the air passages R1 to R4 can flow into the mouth 101 via the front teeth insertion recess 13, and air in the mouth 101 can flow into the air passages R1 to R4 via the front teeth insertion recess 13. The thickness (the dimension in the upper-to-lower direction) of the sandwiching target 10 is preferably set to equal to or greater than 10 mm and equal to or less than 30 mm, but is more preferably set to equal to or greater than 15 mm and equal to or less than 25 mm.

Figure 5:
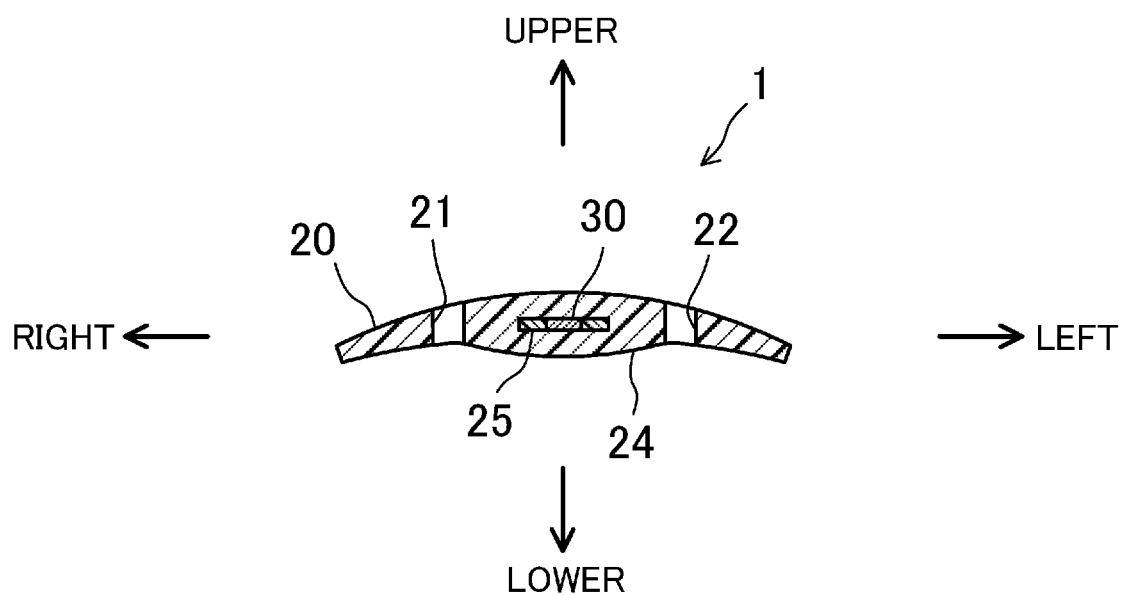
FIG. 5 is a sectional view along an A-A line of FIG. 1.

As illustrated in FIGS. 1 and 2, the dimension of the tongue presser 20 in the right-to-left direction is set longer than the dimension of the sandwiching target 10 in the right-to-left direction. A right end portion of the tongue presser 20 protrudes rightward, and a left end portion of the tongue presser 20 protrudes leftward. The right and left end portions of the tongue presser 20 are molded in a plate shape. Moreover, a center portion of the tongue presser 20 in the right-to-left direction is also in a plate shape. As illustrated in FIG. 5, the center portion of the tongue presser 20 in the right-to-left direction is formed thicker than the right and left end portions. As illustrated in this figure, the center portion of the tongue presser 20 in the right-to-left direction is positioned uppermost, and the tongue presser 20 is gently curved downward as extending toward the right and left end portions. The dimension of the tongue presser 20 in the right-to-left direction can be set to about 30 mm to 40 mm, for example.

As illustrated in FIGS. 1 and 3, multiple right through-holes 21 are, on the right side of the tongue presser 20, formed apart from each other in the front-to-back direction. Moreover, multiple left through-holes 22 are, on the left side of the tongue presser 20, formed apart from each other in the front-to-back direction. The right through-holes 21 and the left through-holes 22 open at upper and lower surfaces of the tongue presser 20. Note that the right through-holes 21 and the left through-holes 22 may be omitted.

A hollow 20a is formed at a far-side end portion of the tongue presser 20 in the direction of insertion into the mouth. The hollow 20a is a portion for preventing or suppressing a far-side edge portion of the tongue presser 20 from contacting the back of the throat, and may be a cutout or a recess, for example. The depth of the hollow 20a can be set to equal to or greater than 5 mm and equal to or less than 10 mm.

As illustrated in FIGS. 5 and 7, the tongue presser 20 includes an outer layer portion 24 made of elastomer, and a core member 25 made of a material harder than the elastomer forming the outer layer portion 24 and embedded in the outer layer portion 24. The core member 25 can be made of a resin material such as polypropylene, but the present invention is not limited to above. For example, the core member 25 may be made of a metal material. The core member 25 preferably exhibits elasticity. The core member 25 is formed in a plate shape, and extends in the front-to-back direction at the center portion of the tongue presser 20 in the right-to-left direction. The strength of the tongue presser 20 can be enhanced by the core member 25, and during sleeping, the tongue 102 can be reliably pushed by the tongue presser 20. The entirety of the core member 25 is embedded in the outer layer portion 24, and therefore, the core member 25 is covered with a soft member. Thus, in a state in which the sleep apnea syndrome symptom improvement aid 1 is inserted into the mouth 101 as illustrated in FIG. 12, the core member 25 does not contact a mucous membrane etc. in the mouth 101.

The front side of the core member 25 may extend until reaching the portion sandwiched by the upper front teeth 110 and the lower front teeth 111. Thus, the position of the core member 25 can be determined with the core member 25 being sandwiched by the upper front teeth 110 and the lower front teeth 111.

In this embodiment, the detector 30 is provided at the tongue presser 20, but the present invention is not limited to above. The detector 30 can be provided at the sandwiching target 10. As illustrated in FIG. 7, the detector 30 is, as in the core member 25, embedded in the outer layer portion 24 of the tongue presser 20. Moreover, the detector 30 is embedded in a middle portion of the core member 25 in the front-to-back direction, and is integrated with the core member 25. The detector 30 is capable of detecting at least one of the vital sign or the salivary component of the patient 100, and a typical well-known detector can be used. The vital sign includes, for example, an oxygen saturation measurement value, a body temperature, a heart rate, a pulse, a blood pressure, a blood oxygen level, etc. upon sleep apnea, and is a signal indicating that a human is alive and indicating whether or not a human is in a normal state. Moreover, the salivary component includes, for example, a biomarker and glucose. The component in the saliva is analyzed, and the level of the biomarker is measured. In this manner, various symptoms can be early discovered. In the saliva, an extremely-small amount of glucose with respect to the blood is contained, and the amount of glucose contained in the saliva is measured so that a blood glucose level can be estimated. That is, the saliva is collected instead of the blood so that diabetes can be diagnosed. Methods described in various academic documents etc. can be used as the method for measuring the biomarker or the glucose. The detector 30 may include, for example, a light emitting body and one configured to generate magnetic force.

Figure 10:
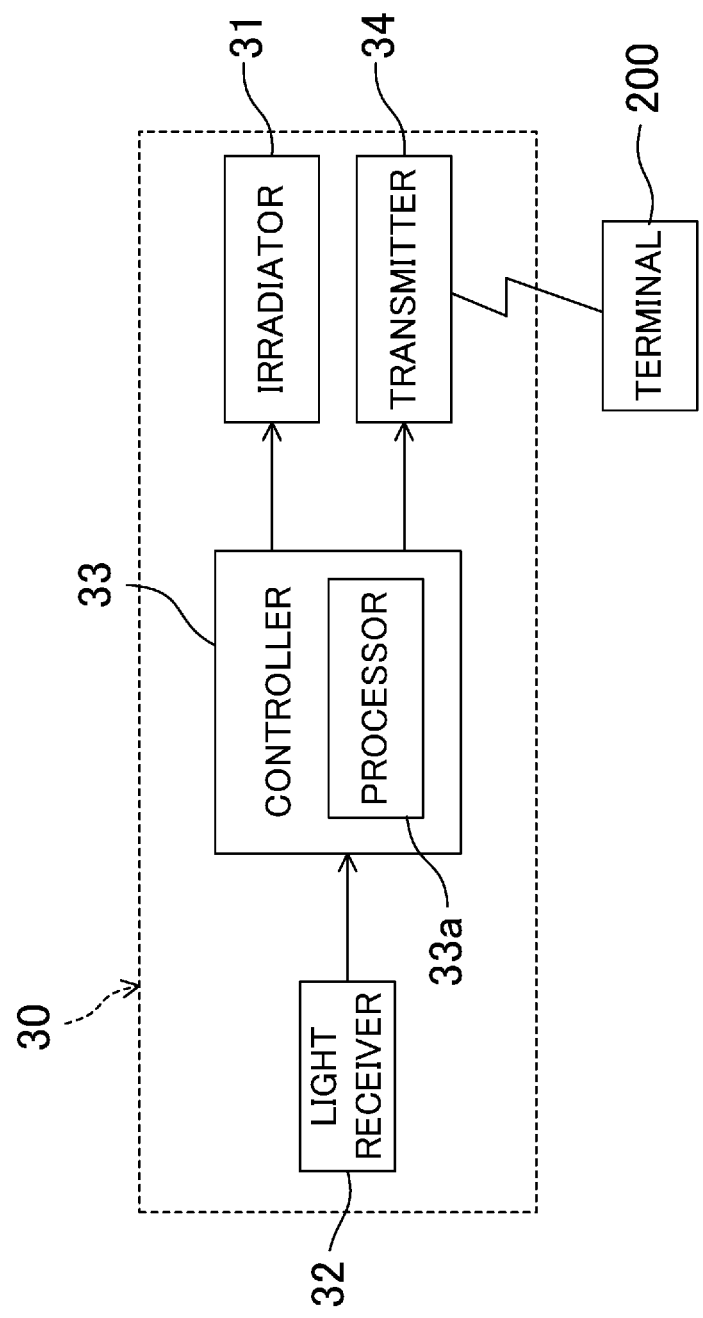
FIG. 10 is a block diagram of a detector.

In the case of measuring the body temperature as the vital sign, it may be configured such that a temperature sensor mounted on, e.g., a well-known thermometer is provided. In the case of measuring the heart rate, the pulse, or the blood oxygen level as the vital sign, it may be configured such that an irradiator 31 configured to irradiate light and a light receiver 32 configured to receive the light irradiated from the irradiator 31 are provided as illustrated in FIG. 10. That is, the detector 30 includes at least the irradiator 31, the light receiver 32, a controller 33, and a transmitter 34. The irradiator 31 may include, for example, an LED configured to irradiate infrared light, and may be a light emitting element typically used for, e.g., blood flow measurement. The light receiver 32 may also include a light receiving element typically used for, e.g., blood flow measurement. The irradiator 31 and the light receiver 32 are arranged facing a surface of the tongue 102.

The controller 33 is configured to cause the irradiator 31 to irradiate measurement light and to obtain the intensity of light received by the light receiver 32 to obtain a blood flow of the tongue 102 based on the intensity of light received by the light receiver 32. For example, the blood flowing in a blood vessel pulsates due to beating of the heart. When such a blood vessel is irradiated with the measurement light by the irradiator 31, the intensity of light received by the light receiver 32 changes according to pulsation of the blood. A processor 33a uses such a change to perform predetermined arithmetic processing, and in this manner, the heart rate, the pulse, or the blood oxygen level can be obtained. Note that the method for measuring the heart rate, the pulse, or the blood oxygen level by light irradiation is used for various types of equipment, and there are various methods. These methods can be used for any configuration of the present embodiment. Note that a power source such as a battery can be built in the controller 33.

The transmitter 34 is a transmission module configured to transmit a detection result of the detector 30 to the outside. For example, the transmitter 34 may be configured to wirelessly transmit the detection result to an external terminal 200, or may be configured to transmit the detection result to the terminal 200 via a wire. The terminal 200 may include, for example, a personal computer, a tablet terminal, and a smartphone.

(Method for Using Sleep Apnea Syndrome Symptom Improvement Aid 1)

As illustrated in FIG. 12, the sleep apnea syndrome symptom improvement aid 1 is inserted into the mouth 101 of the sleep apnea syndrome patient 100. Then, the patient 100 bites the sandwiching target 10 with the upper front teeth 110 and the lower front teeth 111, thereby sandwiching the sandwiching target 10 and fixing the sleep apnea syndrome symptom improvement aid 1. In this state, the lower front teeth 111 are inserted into the front teeth insertion recess 13 of the sandwiching target 10, and therefore, the lower front teeth 111 are fitted in the front teeth insertion recess 13. Accordingly, relative position shift among the sandwiching target 10 and the front teeth 111 is reduced. In this manner, breathing via the air passages R1 to R4 is allowed. When the sleep apnea syndrome symptom improvement aid 1 is fixed in the mouth 101, the tongue presser 20 is positioned to extend to the vicinity of the soft palate 105 of the patient 100, and presses the tongue 102. Thus, even when a posture in bedtime is the supine position, the tongue 102 less moves downward. Thus, the symptom of the sleep apnea syndrome is improved.

A large portion of the sandwiching target 10 is positioned in the mouth 101, and the entirety of the tongue presser 20 is positioned in the mouth 101. Thus, the detector 30 is provided at at least one of the sandwiching target 10 or the tongue presser 20 so that the vital sign such as the pulse or the blood oxygen level can be detected in the mouth 101. Consequently, the state of the patient 100 can be promptly and reliably obtained.

In the case of obtaining the vital sign, the direction of light irradiation by the irradiator 31 may be a direction toward the brain. Such light is received and subjected to the arithmetic processing, and in this manner, the blood flow in the brain can be measured.

The salivary glands for saliva secretion include the large salivary glands, such as the sublingual gland and the submandibular gland, positioned around the mouth 101 into which the sleep apnea syndrome symptom improvement aid 1 is to be inserted, the tongue 102, and the cheek; and the small salivary glands, such as the labial gland, the cheek gland, the palatal gland, the molar gland, and the tongue gland, numerously dispersed at the mucous membrane of the mouth and also called mucous glands. The sleep apnea syndrome symptom improvement aid 1 inserted into the mouth 101 exhibits elasticity, and therefore, slightly changes the form thereof in the mouth by movement of, e.g., the tongue 102 or the teeth. Thus, the sleep apnea syndrome symptom improvement aid 1 stimulates the small salivary glands broadly dispersed across the lip 112, the cheek, the tongue 102, and the palate, and therefore, salivation easily occurs. Consequently, the saliva can provide advantageous effects such as food digestion, friction prevention/protection of the mucous membrane, abrasion prevention/protection of the teeth, reduction of cavities and periodontal diseases by self-cleaning action, reduction of bacteria, prevention of lowering of taste recognition, and prevention of xerostomia.

Second Embodiment

Figure 13:
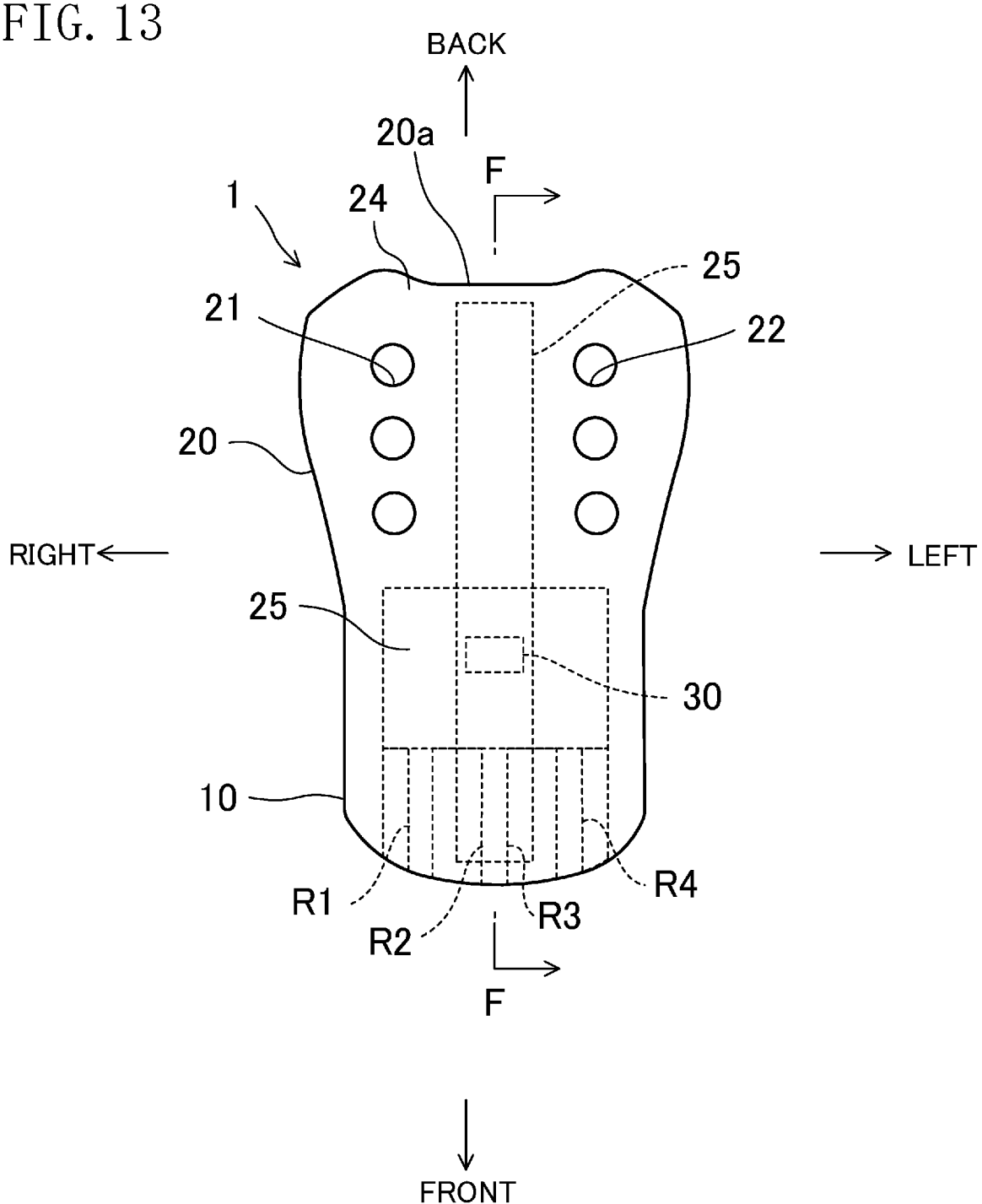
FIG. 13 is a view of a second embodiment, FIG. 13 corresponding to FIG. 1.
Figure 14:
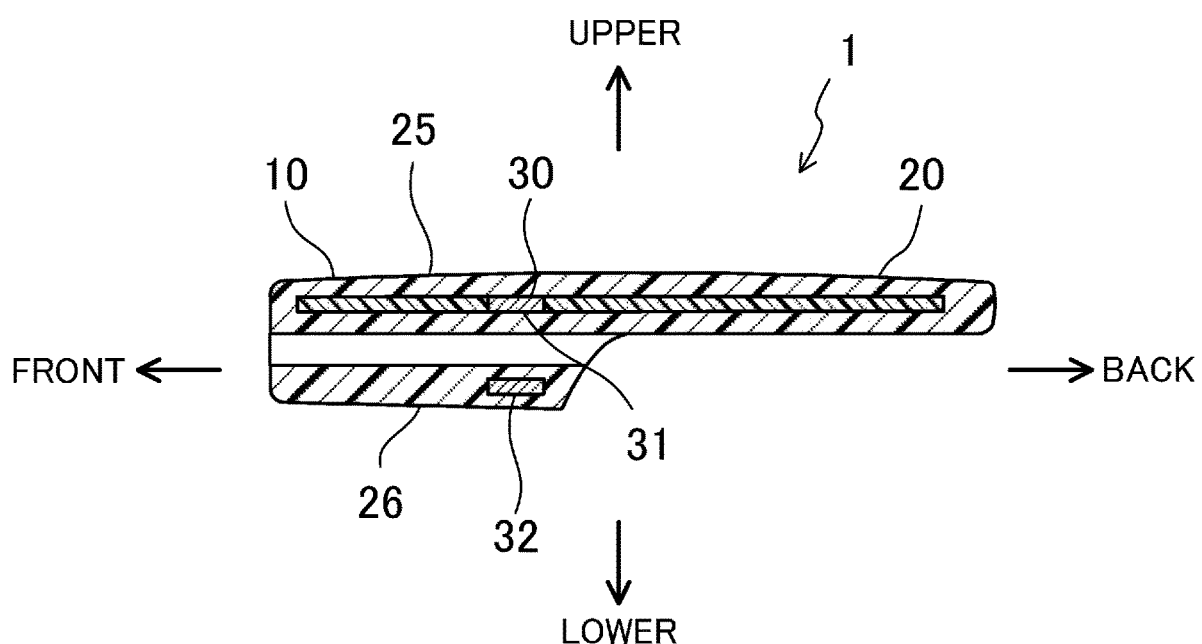
FIG. 14 is a sectional view along an F-F line of FIG. 14.
Figure 15:
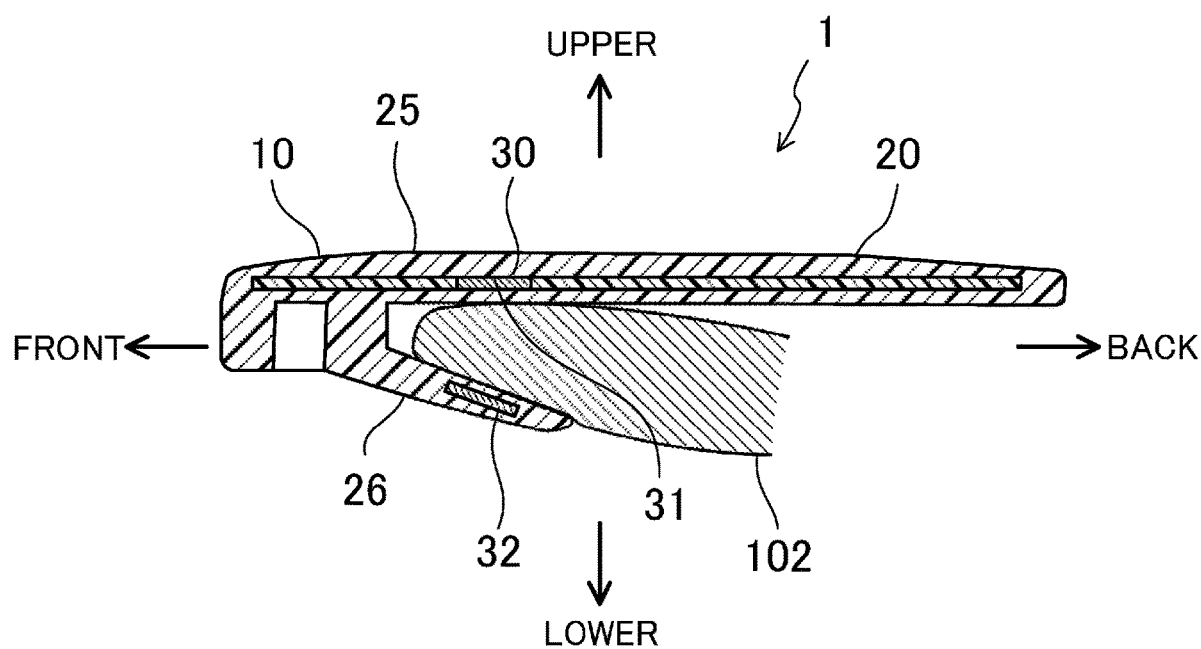
FIG. 15 is a view of a tongue insertion state, FIG. 15 corresponding to FIG. 14.

FIGS. 13 to 15 illustrate a sleep apnea syndrome symptom improvement aid 1 according to a second embodiment of the present invention. The second embodiment is different from the first embodiment in that the tongue 102 can be inserted into the sleep apnea syndrome symptom improvement aid 1. Hereinafter, the same reference numerals are used to represent elements identical to those of the first embodiment, and description thereof will be omitted. Differences will be described in detail.

In the second embodiment, a tongue presser 20 is formed forward with respect to a center portion of the sleep apnea syndrome symptom improvement aid 1 in the front-to-back direction. As illustrated in FIG. 15 etc., the tongue presser 20 has a pressing plate portion 25 arranged above the tongue 102, and a lower plate portion 26 arranged below the tongue 102. As illustrated in FIG. 14, in a state in which the sleep apnea syndrome symptom improvement aid 1 is taken out of the mouth 101, a spacing between the pressing plate portion 25 and the lower plate portion 26 is set such that a predetermined clearance is formed between the pressing plate portion 25 and the lower plate portion 26. Moreover, a space between the pressing plate portion 25 and the lower plate portion 26 opens to the back side of the sleep apnea syndrome symptom improvement aid 1. The tongue 102 is inserted into such an opening portion from a tip end side. In this manner, the lower plate portion 26 can be elastically deformed downward, and the tongue 102 can be inserted into the space between the pressing plate portion 25 and the lower plate portion 26.

An irradiator 31 of a detector 30 is arranged at the pressing plate portion 25. Moreover, a light receiver 32 of the detector 30 is arranged at the lower plate portion 26. Conversely, the irradiator 31 of the detector 30 may be arranged at the lower plate portion 26, and the light receiver 32 of the detector 30 may be arranged at the pressing plate portion 25. In the second embodiment, light irradiated from the irradiator 31 is received by the light receiver 32 through the tongue 102.

In the case of the second embodiment, a symptom of a sleep apnea syndrome can be, as in the first embodiment, improved while a vital sign of a patient 100 can be obtained.

Third Embodiment

Figure 16:
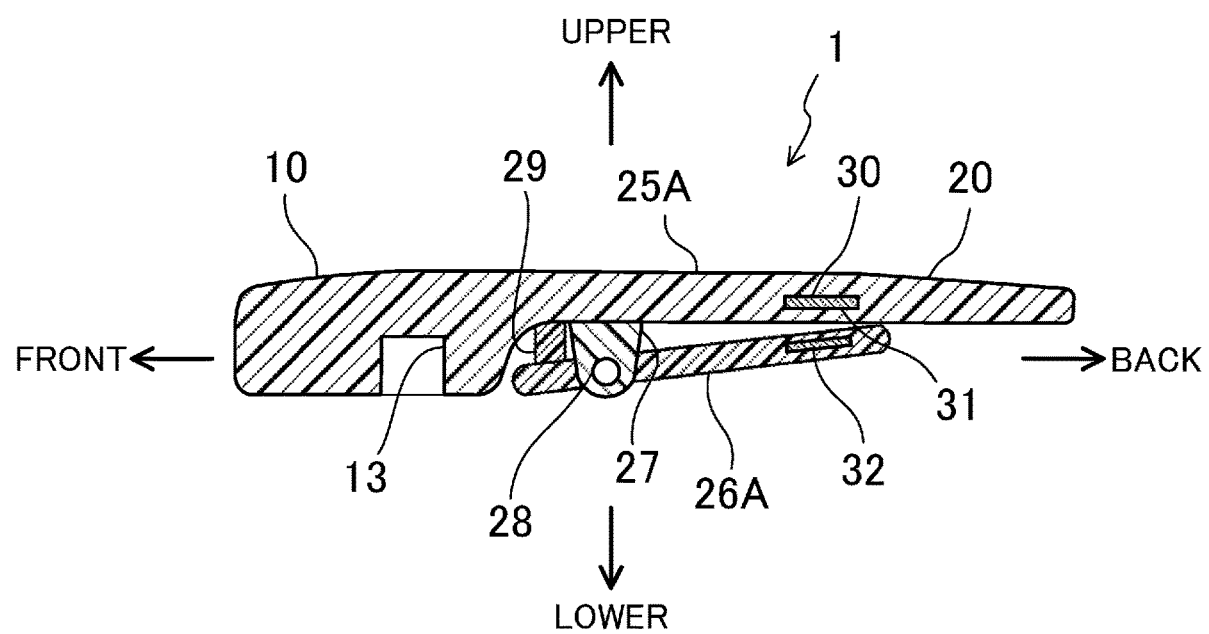
FIG. 16 is a view of a third embodiment, FIG. 16 corresponding to FIG. 14.
Figure 17:
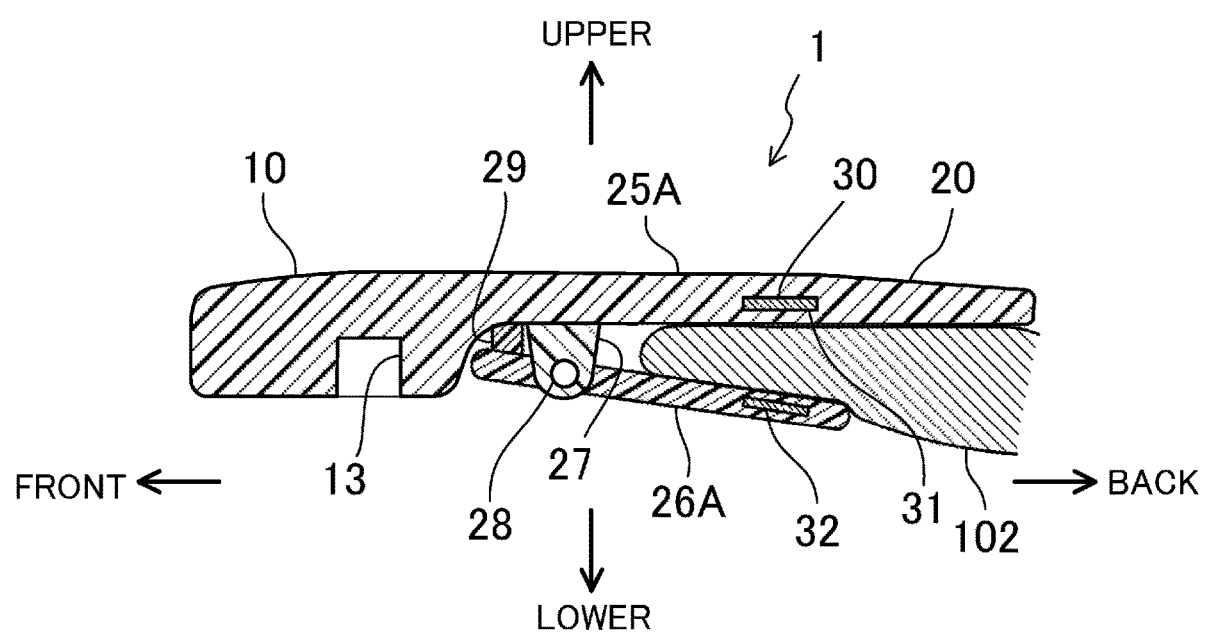
FIG. 17 is a view of the third embodiment, FIG. 17 corresponding to FIG. 15.

FIGS. 16 and 17 illustrate a sleep apnea syndrome symptom improvement aid 1 according to a third embodiment of the present invention. The third embodiment is different from the first embodiment in that the tongue 102 can be sandwiched in the upper-to-lower direction. Hereinafter, the same reference numerals are used to represent elements identical to those of the first embodiment, and description thereof will be omitted. Differences will be described in detail.

A tongue presser 20 includes a pressing plate portion 25A arranged above the tongue 102, and a lower plate portion 26A arranged below the tongue 102. The lower plate portion 26A is formed as a member separated from the pressing plate portion 25A. Further, the tongue presser 20 includes a support shaft 28 swingably supporting the lower plate portion 26A in the upper-to-lower direction, and a biasing member 29 configured to bias the lower plate portion 26A in the direction of pushing the lower plate portion 26A against the lower side of the tongue 102. The support shaft 28 is supported at a receiving portion 27 fixed to a lower surface of the pressing plate portion 25A. A front end side of the lower plate portion 26A is supported by the support shaft 28. For example, the lower plate portion 26A is, by finger force, swung against biasing force of the biasing member 29 in the direction of moving a back end side of the lower plate portion 26A away from the pressing plate portion 25A. In this manner, a clearance into which the tongue 102 can be inserted is formed between the lower plate portion 26A and the pressing plate portion 25A. After insertion of the tongue 102, when a finger is released, the lower plate portion 26A and the pressing plate portion 25A sandwich the tongue 102 by the biasing force of the biasing member 29. Thus, a relative position relationship between the tongue 102 and the sleep apnea syndrome symptom improvement aid 1 less shifts, and the effect of improving a symptom of a sleep apnea syndrome is enhanced. Moreover, the accuracy of detection of a vital sign is also enhanced. Although not shown in the figure, a core member extending in the front-to-back direction may be provided at the lower plate portion 26A. Moreover, the biasing member 29 may include, for example, a coil spring and an elastic member such as rubber.

In the case of the third embodiment, the symptom of the sleep apnea syndrome can be, as in the first embodiment, improved while the vital sign of a patient 100 can be obtained.

Figure 18:
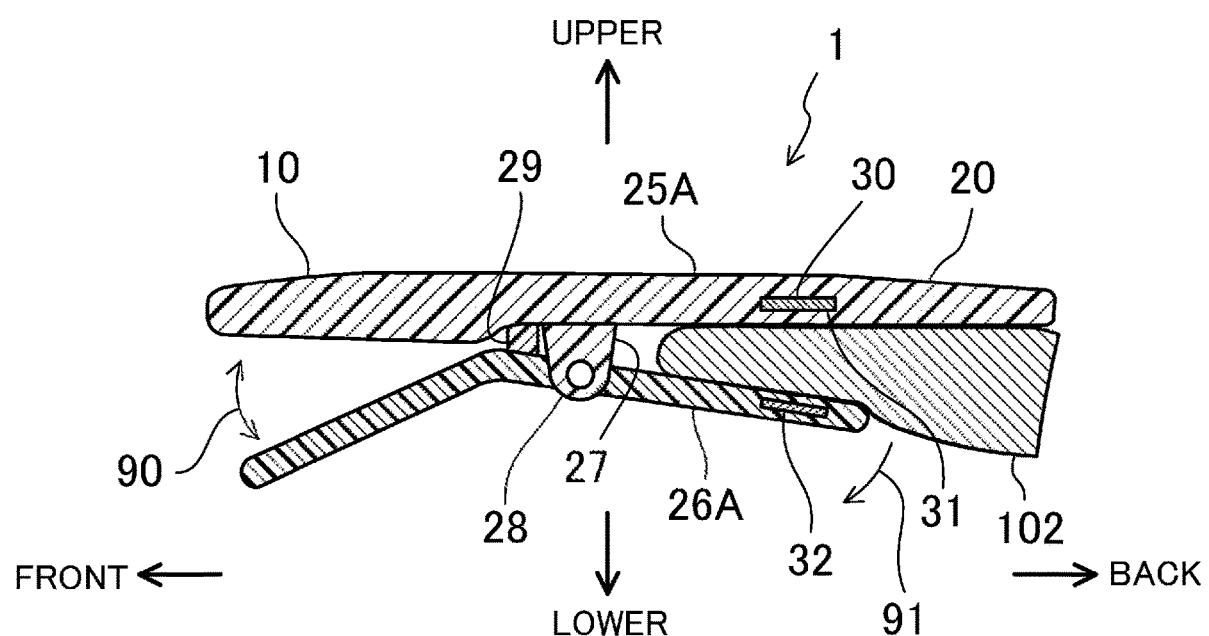
FIG. 18 is a view of a variation of the third embodiment, FIG. 18 corresponding to FIG. 17.
Figure 19:
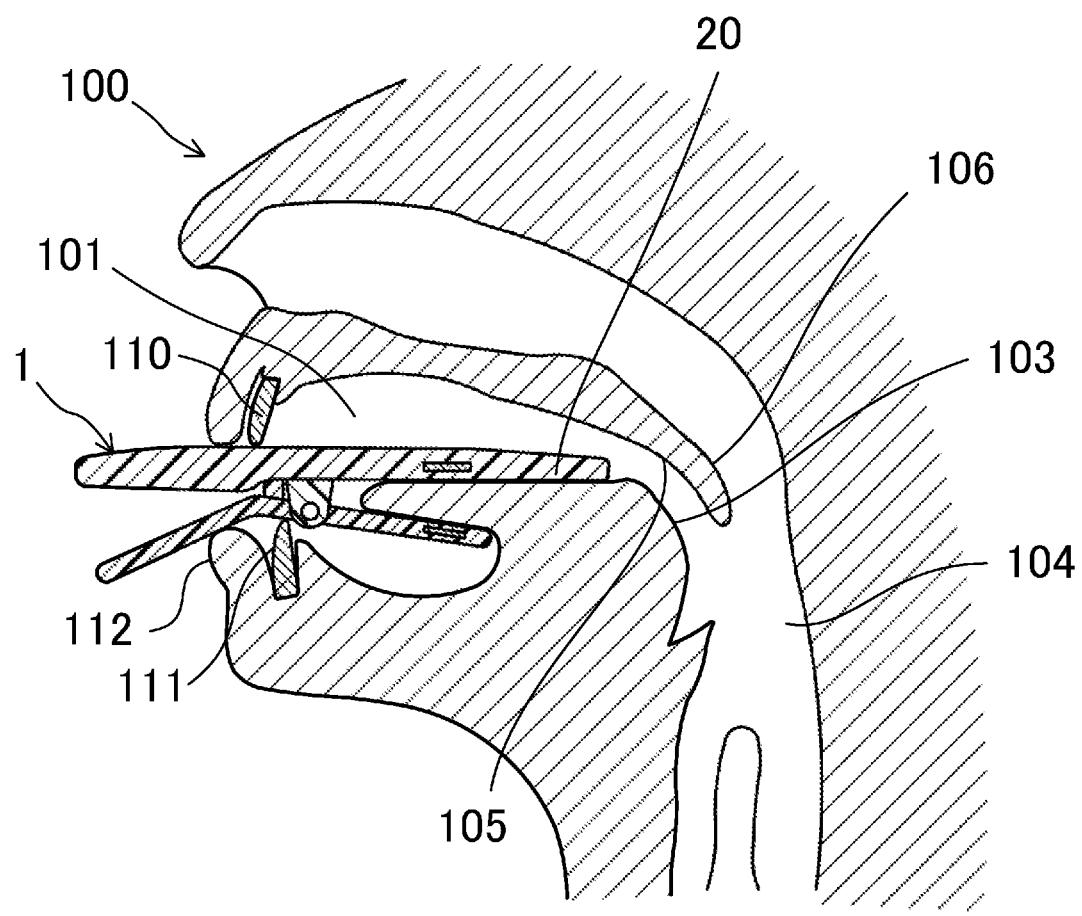
FIG. 19 is a view of a variation of the third embodiment, FIG. 19 corresponding to FIG. 12.

Moreover, as in a variation of the third embodiment illustrated in FIGS. 18 and 19, the near sides (the front sides) of the pressing plate portion 25A and the lower plate portion 26A may be extended to protrude to the outside of the mouth 101 from the lip 112. In this variation, the near side of the lower plate portion 26A is swung in the direction of an arrow 90 illustrated in FIG. 18 so that the lower plate portion 26A can switch between a state in which the tongue 102 is sandwiched by the pressing plate portion 25A and the lower plate portion 26A and a state (a non-sandwiching state) in which the tongue 102 is not sandwiched. The pressing plate portion 25A and the lower plate portion 26A protrude to the outside of the mouth 101, and therefore, operation can be facilitated.

Fourth Embodiment

Figure 20:
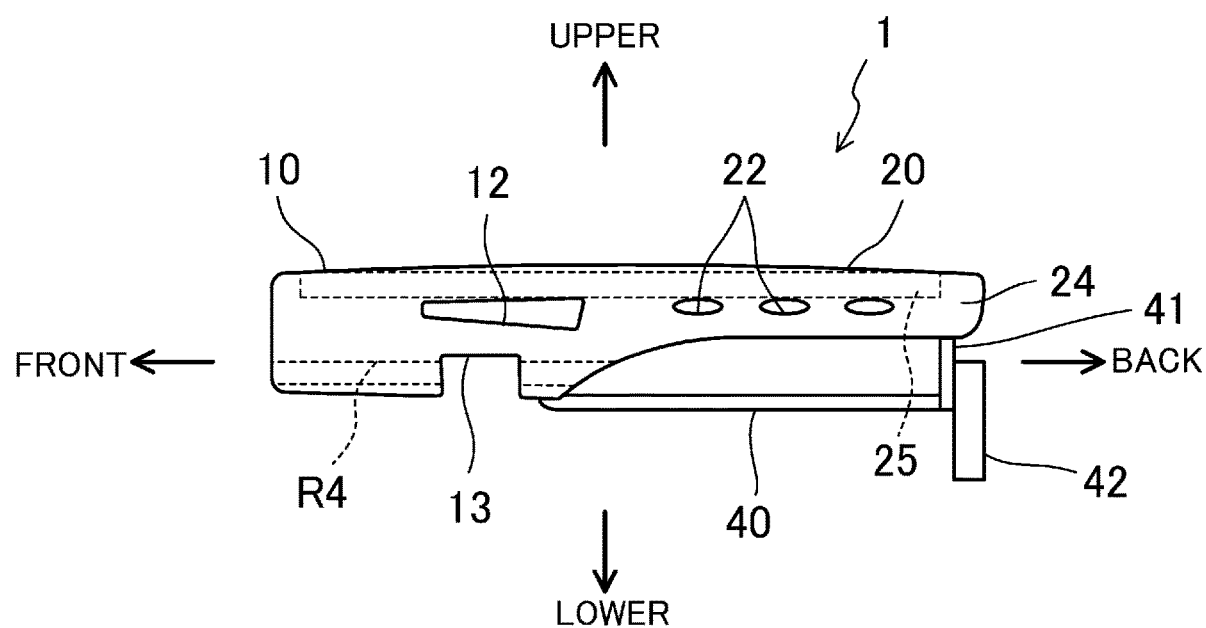
FIG. 20 is a view of a fourth embodiment, FIG. 20 corresponding to FIG. 2.

FIG. 20 illustrates a sleep apnea syndrome symptom improvement aid 1 according to a fourth embodiment of the present invention. The fourth embodiment is different from the first embodiment in that a portion contacting the tongue 102 is in a bridge shape. Hereinafter, the same reference numerals are used to represent elements identical to those of the first embodiment, and description thereof will be omitted. Differences will be described in detail.

A plate-shaped portion 40 including an elastic member extending from a sandwiching target 10 to the back side is provided below a tongue presser 20. The plate-shaped portion 40 is arranged apart from a body portion of the tongue presser 20 below the tongue presser 20, and is configured elastically deformable in the upper-to-lower direction. A back end portion of the plate-shaped portion 40 reaches the vicinity of a back end portion of the tongue presser 20. At a back end portion of the body portion of the tongue presser 20, a back end support portion 41 is provided to protrude downward. The back end portion of the plate-shaped portion 40 is fixed to a lower end portion of the back end support portion 41. Thus, in a state in which the sleep apnea syndrome symptom improvement aid 1 is inserted into the mouth 101, the tongue 102 contacts a lower surface of the plate-shaped portion 40. By pressing force of the tongue 102, the plate-shaped portion 40 is elastically deformed to bend upward, and turns into a shape along the tongue 102. Moreover, a tubular holding portion 42 configured to hold a pipe etc. (not shown) may be provided at the back end portion of the back end support portion 41 or the plate-shaped portion 40. The pipe etc. are inserted into and held by the holding portion 42 so that the positions of the pipe etc. can be determined at predetermined positions.

In the case of the fourth embodiment, a symptom of a sleep apnea syndrome can be, as in the first embodiment, improved while a vital sign of a patient 100 can be obtained.

Fifth Embodiment

Figure 21:
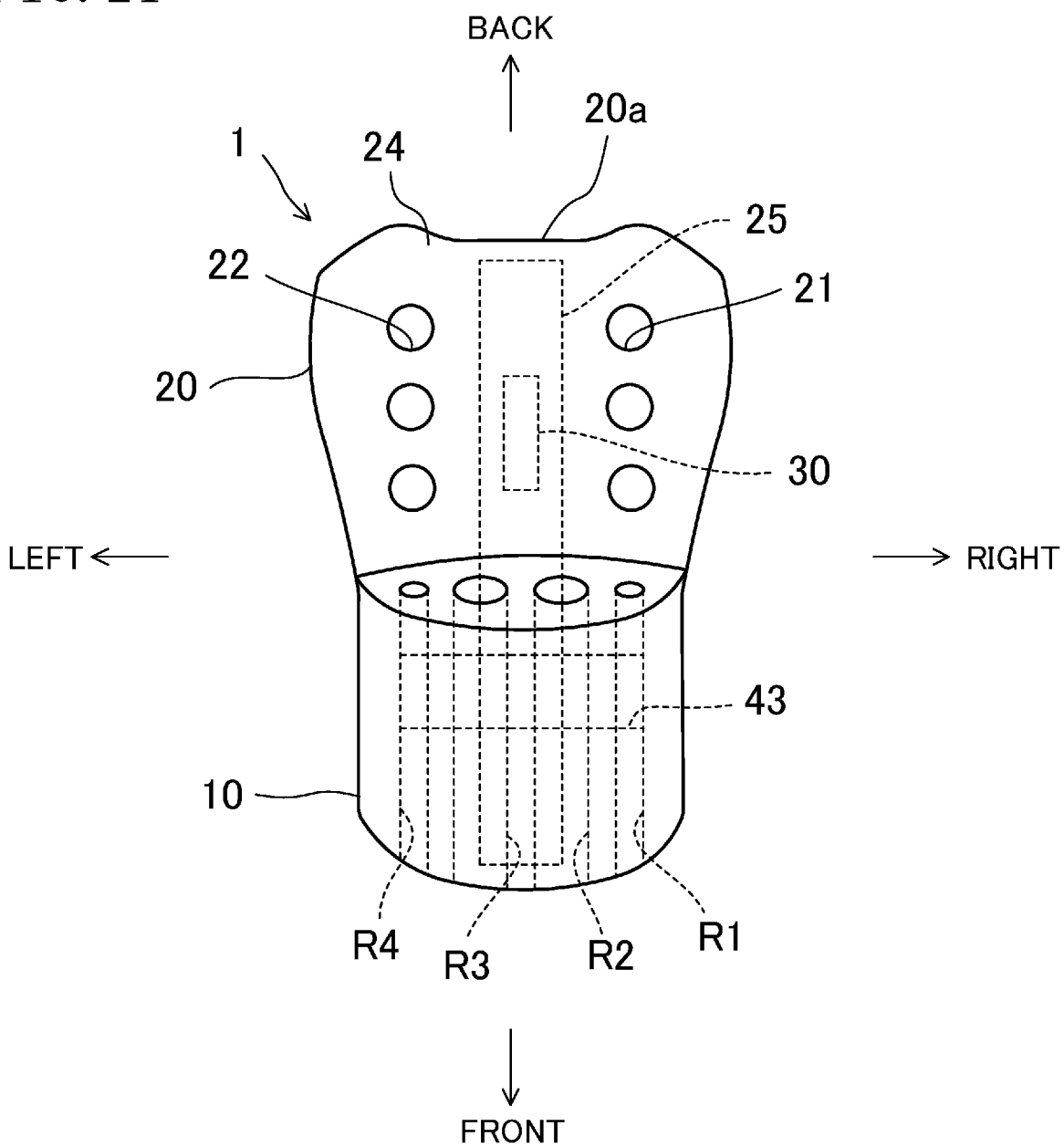
FIG. 21 is a view of a fifth embodiment, FIG. 21 corresponding to FIG.
Figure 22:
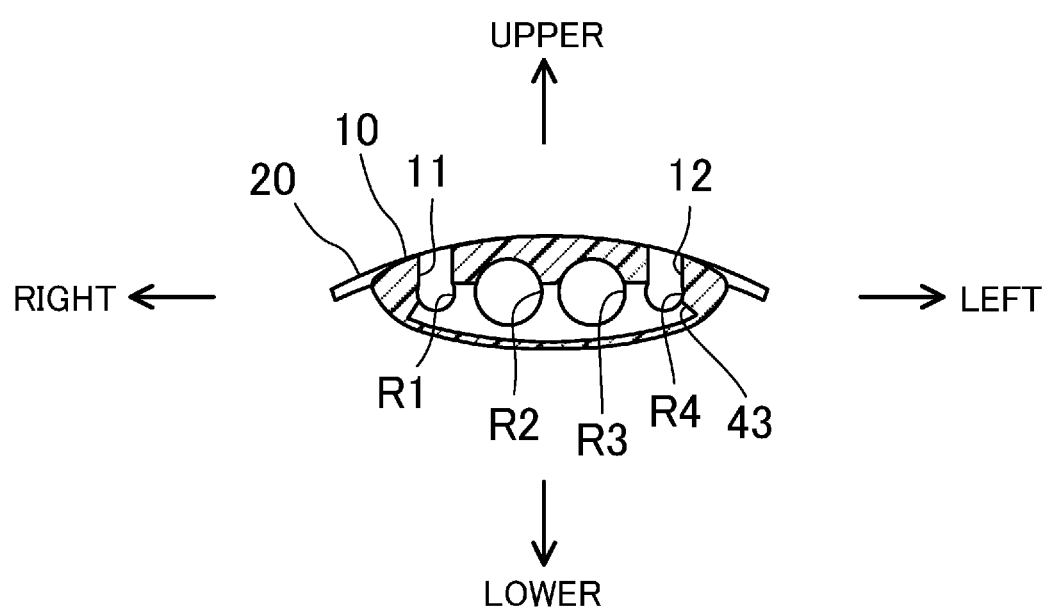
FIG. 22 is a view of the fifth embodiment, FIG. 22 corresponding to FIG. 6.

FIGS. 21 and 22 illustrate a sleep apnea syndrome symptom improvement aid 1 according to a fifth embodiment of the present invention. In the fifth embodiment, a hollow space 43 is provided instead of a front teeth insertion recess 13. Hereinafter, the same reference numerals are used to represent elements identical to those of the first embodiment, and description thereof will be omitted. Differences will be described in detail.

That is, in the fifth embodiment, the hollow space 43 is formed at a portion where the front teeth insertion recess 13 of the first embodiment is formed. As illustrated in FIG. 22, the hollow space 43 is covered with a material forming a sandwiching target 10. In a state in which the sleep apnea syndrome symptom improvement aid 1 is inserted into the mouth 101, the front teeth 110, 111 sandwich a portion corresponding to the hollow space 43. In this state, the lower front teeth 111 elastically and upwardly deform an outer layer of the portion corresponding to the hollow space 43. Thus, the positions of the lower front teeth 111 are determined by the hollow space 43, and therefore, position shift less occurs.

In the case of the fifth embodiment, a symptom of a sleep apnea syndrome can be, as in the first embodiment, improved while a vital sign of a patient 100 can be obtained.

Note that a detector 30 may be separated from the sandwiching target 10 or a tongue presser 20. The detector 30 may be used with the detector 30 being inserted into the sandwiching target 10 or the tongue presser 20, and may be used integrally with the sandwiching target 10 or the tongue presser 20.

Figure 23:
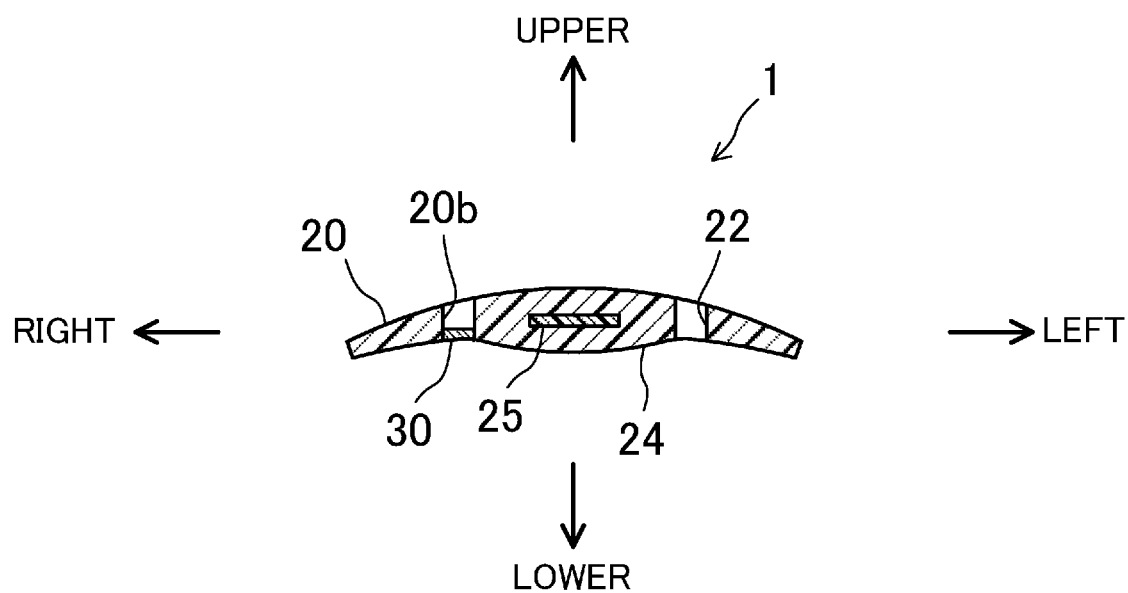
FIG. 23 is a view of another variation, FIG. 23 corresponding to FIG. 5.

As in a variation illustrated in FIG. 23, a saliva reservoir 20b in which the saliva is accumulated may be provided at the tongue presser 20, and the detector 30 configured to detect a salivary component may be provided at the saliva reservoir 20b. The saliva reservoir 20b includes a hollow or a recess opening at an upper surface of the tongue presser 20. In bedtime, the saliva of a patient 100 is accumulated in the saliva reservoir 20b. The detector 30 is provided facing an inner surface of the saliva reservoir 20b, and is arranged to reliably contact the saliva accumulated in the saliva reservoir 20b. According to this configuration, the saliva component (e.g., protein, carb, fat, glucose, and various tumor markers) can be reliably detected.

Figure 24:
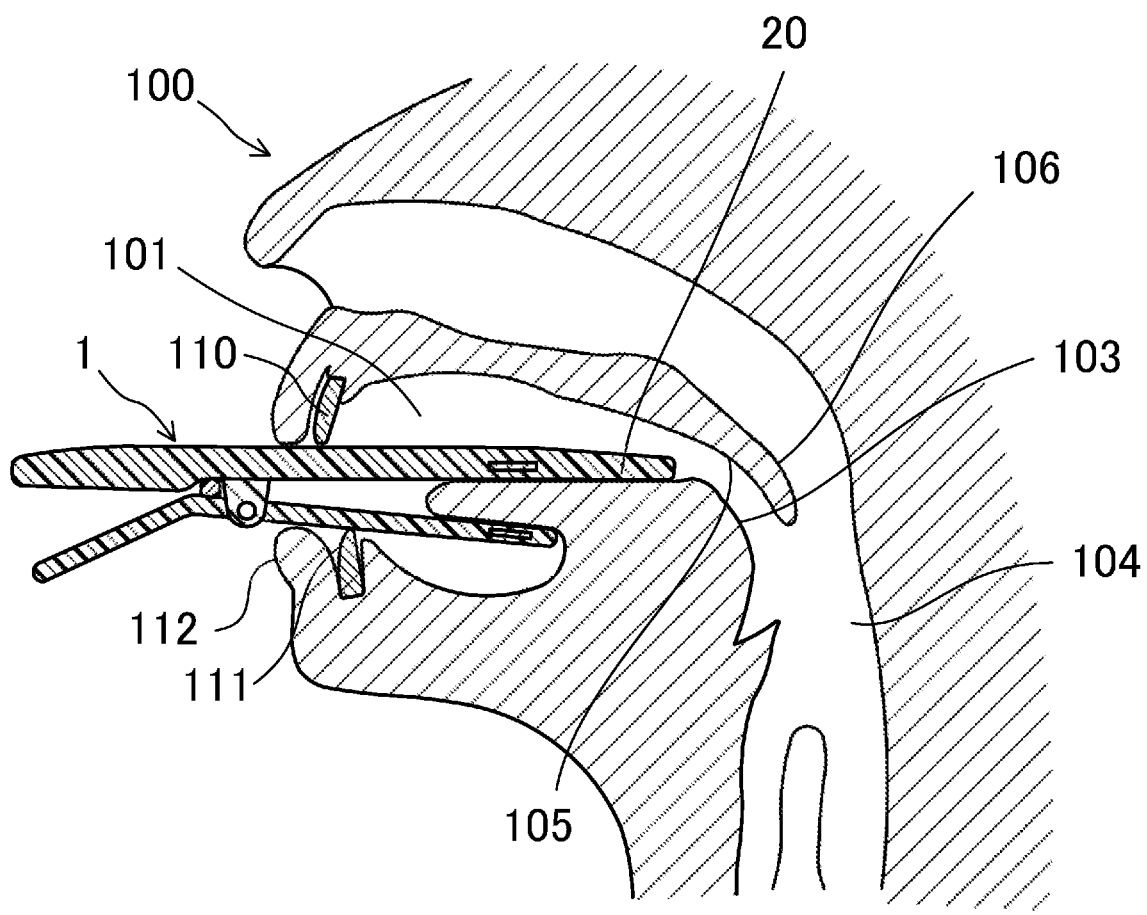
FIG. 24 is a view of a first insertion state, FIG. 24 corresponding to FIG. 12.

As illustrated in FIG. 24, the sleep apnea syndrome symptom improvement aid 1 can be inserted into the mouth 101 of the sleep apnea syndrome patient 100 such that an operation portion of the sleep apnea syndrome symptom improvement aid 1 protrudes to the outside of the mouth 101. Thus, a user can easily operate the operation portion of the sleep apnea syndrome symptom improvement aid 1.

Figure 25:
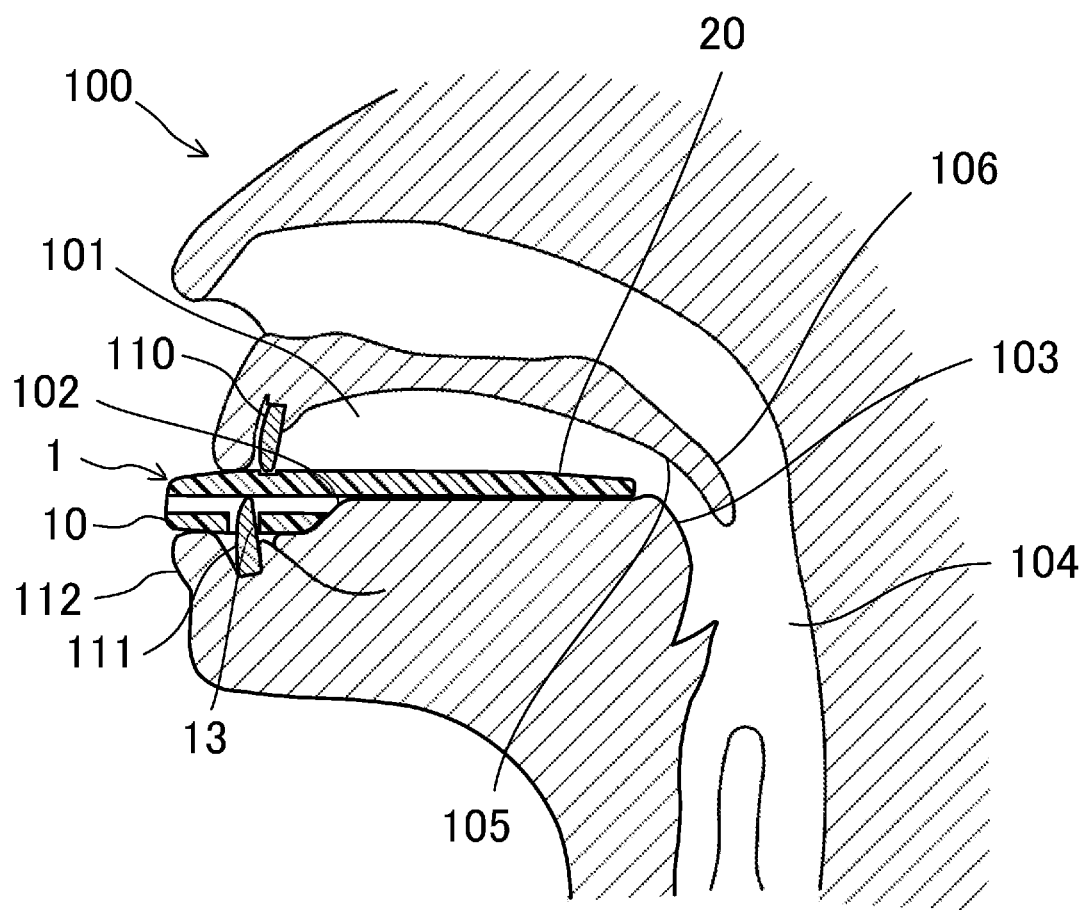
FIG. 25 is a view of a second insertion state, FIG. 25 corresponding to FIG. 12.

As illustrated in FIG. 25, a front teeth insertion recess 13 into which the lower front teeth 111 of the patient 100 are to be inserted may be moved forward. In this case, when the sleep apnea syndrome symptom improvement aid 1 is inserted into the mouth 101 of the sleep apnea syndrome patient 100, the lower jaw moves forward such that the lower front teeth 111 are forward of the upper front teeth 110. Thus, a symptom of a sleep apnea syndrome can be more effectively improved.

Figure 26:
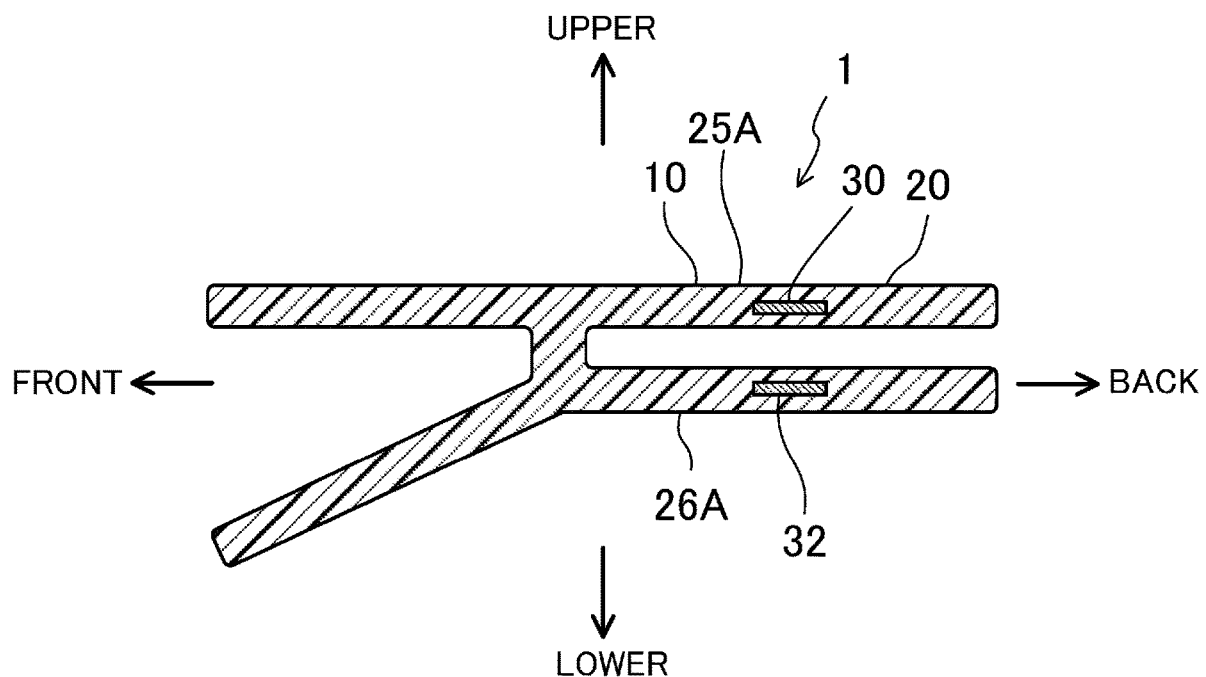
FIG. 26 is a view of an integrally-molded type, FIG. 26 corresponding to FIG. 14.

As illustrated in FIG. 26, in the case of a configuration in which the tongue 102 can be sandwiched in the upper-to-lower direction, a pressing plate portion 25A and a lower plate portion 26A may be integrally molded. In this case, a coupling portion between the pressing plate portion 25A and the lower plate portion 26A can be provided between the pressing plate portion 25A and the lower plate portion 26A. When the pressing plate portion 25A and the lower plate portion 26A are opened, portions of the pressing plate portion 25A and the lower plate portion 26A positioned outside the mouth 101 are operated. Thus, the coupling portion is mainly elastically deformed, and a spacing between the pressing plate portion 25A and the lower plate portion 26A is expanded. External force in an opening direction is eliminated so that the tongue 102 can be sandwiched in the upper-to-lower direction by the pressing plate portion 25A and the lower plate portion 26A.

On any points, the above-described embodiments have been set forth merely as examples, and shall not be interpreted in a limited manner. Further, variations and changes belonging to an equivalent scope of the scope of the claims are all within the scope of the present invention.

INDUSTRIAL APPLICABILITY

As described above, the sleep apnea syndrome symptom improvement aid according to the present invention can be used for the patient of the sleep apnea syndrome.

DESCRIPTION OF REFERENCE CHARACTERS

1 Sleep Apnea Syndrome Symptom Improvement Aid
10 Sandwiching Target
13 Front Teeth Insertion Recess
20 Tongue Pressing Portion
30 Detector
31 Irradiator
32 Light Receiver
33 Controller
33a Processor
34 Transmitter
100 Patient
101 Mouth
102 Tongue
200 Terminal
R1 to R4 Air Passage

The invention claimed is:

1. A sleep apnea syndrome symptom improvement aid to be inserted into a mouth of a sleep apnea syndrome patient, comprising:
 a sandwiching target configured to be sandwiched by upper and lower front teeth of the patient and which includes an elastic body arranged facing an outside of the mouth from a lip and having an air passage extending from a front end portion to an inside of the mouth;
 a tongue presser extending from the sandwiching target to a vicinity of a soft palate of the patient and including an elastic body configured to press a tongue; and
 a detector provided at at least one of the sandwiching target or the tongue presser and configured to detect at least one of a vital sign or a salivary component of the patient,
 wherein
 the tongue presser includes a core member and an outer layer portion made of elastomer, and
 the core member is made of a material harder than the elastomer forming the outer layer portion, and is embedded in the outer layer portion.

2. The sleep apnea syndrome symptom improvement aid according to claim 1, wherein
 the sandwiching target is provided with a recess into which the front teeth are to be inserted.

3. The sleep apnea syndrome symptom improvement aid according to claim 1, wherein
 the detector is provided at the tongue presser.

4. The sleep apnea syndrome symptom improvement aid according to claim 1, further comprising:
 a transmitter configured to transmit a detection result of the detector to an outside.

5. The sleep apnea syndrome symptom improvement aid according to claim 1, wherein
 the tongue presser is provided with a saliva reservoir configured to accumulate saliva, and
 the detector configured to detect the salivary component is provided at the saliva reservoir.

6. A sleep apnea syndrome symptom improvement aid to be inserted into a mouth of a sleep apnea syndrome patient, comprising:
 a sandwiching target configured to be sandwiched by upper and lower front teeth of the patient and which includes an elastic body arranged facing an outside of the mouth from a lip and having an air passage extending from a front end portion to an inside of the mouth;
 a tongue presser extending from the sandwiching target to a vicinity of a soft palate of the patient and including an elastic body configured to press a tongue; and
 a detector provided at at least one of the sandwiching target or the tongue presser and configured to detect at least one of a vital sign or a salivary component of the patient,
 wherein
 the detector is provided at the tongue presser, and
 the tongue presser includes a pressing plate portion configured to be arranged above the tongue, and a lower plate portion configured to be arranged below the tongue.

7. The sleep apnea syndrome symptom improvement aid according to claim 6, wherein
 the detector includes
 an irradiator arranged at one of the pressing plate portion or the lower plate portion and configured to irradiate the tongue with light, and
 a light receiver arranged at the other one of the pressing plate portion or the lower plate portion and configured to receive the light irradiated from the irradiator, and
 the detector is configured to obtain a blood flow of the tongue based on an intensity of light received by the light receiver.

8. The sleep apnea syndrome symptom improvement aid according to claim 6, wherein
 the tongue presser includes a support rod configured to swingably support the lower plate portion in an upper-to-lower direction, and a biasing member configured to bias the lower plate portion in a direction of pressing the lower plate portion against a lower side of the tongue.

* * * * *